United States Patent
Jiang et al.

(10) Patent No.: US 10,100,343 B2
(45) Date of Patent: Oct. 16, 2018

(54) CRZ1 MUTANT FUNGAL CELLS

(71) Applicant: MERCK SHARP & DOHME CORP., Rahway, NJ (US)

(72) Inventors: Bo Jiang, Norwich, VT (US); Jun Zhuang, Wellesly, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/243,268

(22) Filed: Aug. 22, 2016

(65) Prior Publication Data
US 2016/0355860 A1 Dec. 8, 2016

Related U.S. Application Data

(63) Continuation of application No. 14/437,405, filed as application No. PCT/US2013/065443 on Oct. 17, 2013, now abandoned.

(60) Provisional application No. 61/716,670, filed on Oct. 22, 2012.

(51) Int. Cl.
| | |
|---|---|
| *C12P 21/00* | (2006.01) |
| *C07K 16/00* | (2006.01) |
| *C12N 15/81* | (2006.01) |
| *C07K 14/39* | (2006.01) |
| *C12N 15/80* | (2006.01) |
| *C12P 21/02* | (2006.01) |

(52) U.S. Cl.
CPC ............. *C12P 21/00* (2013.01); *C07K 14/39* (2013.01); *C07K 16/00* (2013.01); *C12N 15/80* (2013.01); *C12N 15/81* (2013.01); *C12N 15/815* (2013.01); *C12P 21/02* (2013.01); *C07K 2317/14* (2013.01)

(58) Field of Classification Search
CPC ...... C12N 15/815; C12N 15/80; C12N 15/81; C07K 2317/14; C07K 14/39; C07K 16/00; C07K 16/241; C07K 2317/21; C07K 2317/33; C07K 2317/41; C07K 2317/52; C07K 2317/622; C07K 2317/76; C07K 2317/92; C12P 21/00; C12P 21/02; A61K 2039/505; A61K 39/3955; A61K 45/06

See application file for complete search history.

(56) References Cited

U.S. PATENT DOCUMENTS

2012/0184020 A1 7/2012 Picataggio et al.
2014/0302557 A1* 10/2014 Jiang ...................... C12N 15/80 435/69.1

FOREIGN PATENT DOCUMENTS

| WO | WO2012145596 | 10/2012 |
| WO | WO201362940 | 5/2013 |

OTHER PUBLICATIONS

Angelike M. Stathopoulos and Martha S. Cyert, Calcineurin acts through the CRZ1/TCN1-encoded transcription factor to regulate gene expression in yeast, Genes Dev, 1997, 3432-3444, 11.
Cyert MS, Calcineurin signaling in *Saccharomyces cerevisiae*: how yeast go crazy in response to stress., Biochem Biophys Res Commun., 2003, 1143-1150, 311(4).
Deschutter, Genome sequence of the recombinant protein production host pichia pastoris, Nat. Biotechnol., 2009, 561-555, 27.
Karababa et al., CRZ1, a target of the calcineurin pathway in Candida albicans, Mol. Microbiol., 2006, 1429-1451, 59(5).
Matheos DP, Kingsbury TJ, Ahsan US, Cunningham KW, Tcn1p/Crz1p, a calcineurin-dependent transcription factor that differentially regulates gene expression in *Saccharomyces cerevisiae*., Genes Dev., 1997, 3445-3458, 11.
Panadero J1, Hernández-López MJ, Prieto JA, Randez-Gil F., Overexpression of the calcineurin target CRZ1 provides freeze tolerance and enhances the fermentative capacity of baker's yeast., Appl Environ Microbiol., 2007, 4824-4831, 73(15).
Lu et al., PLOS ONE, Lack of Trehalose Accelerates H2O2-Induced Candida albicans Apoptosis through Regulating Ca2+ Signaling Pathway and Caspase Activity vol. 6, No. 1, 2011 XP055258010, p. e15808.
Database Accession F2QR79XP055258008, 2011, Retrieved from EBI accession No. UNIPROT.F2QR79 Database.
Fang et al., The role of three calcineurin subunits and a related transcription factor (Crz1) in conidiation, multistress tolerance and virulence in Beauveria bassiana, Applied Microbiology and Biotechnology, vol. 99, No. 2, 2014, pp. 827-840.
Spielvogel, A., In: Environmental stress response in filamentous fungi: the impact of ion homeostasis on gene regulation. Dissertation, Berlin, pp. 1-117 & Appendix, 2008.
Kuberl et al., High Quality Genome Sequence of Pichia Pastoris CBS7435, J. Biotechnol., 2011, No. 4, pp. 312-320, vol. 154.
Wang et al., Alkaline Stress Triggers an Immediate Calcium Fluctuation in Candida Albicans Mediated by Rim101p and Crz1p Transcription Factors, FEMS Yeast Res., 2011, pp. 430-439, vol. 11.

\* cited by examiner

*Primary Examiner* — Sarvamangala Devi
(74) *Attorney, Agent, or Firm* — John David Reilly; Laura M. Ginkel

(57) ABSTRACT

The present invention provides CRZ1 mutant fungal host cells, such as *Pichia pastoris*. The mutant fungal host cells exhibit temperature-resistance, enhanced fermentation robustness and increased expression of heterologous polypeptides such as immunoglobulins. Methods for producing heterologous polypeptides, such as immunoglobulins, using such mutant fungal host cells are within the scope of the present invention.

4 Claims, 12 Drawing Sheets
Specification includes a Sequence Listing.

Deep Sequencing of Temperature-Resistant Mutants
Identified Multiple Mutations in Pp02g02120,
and in Combination with Pp01g00680 (ATT1) Mutations

| Chromosome | yGLY28997 | yGLY29012 | yGLY29010 | yGLY29042 | yGLY28998 | yGLY17159 | yGLY28999 | yGLY29030 | yGLY29031 | ref | read | gene-id | ref | read | ref-a.a | read a.a |
|---|---|---|---|---|---|---|---|---|---|---|---|---|---|---|---|---|
| chr1 | − | − | − | − | − | + | − | − | − | T | TGAATC | Pp01g00680 | T | TGAATC | frame- | shift |
| chr1 | − | − | − | − | + | − | − | − | − | C | T | Pp01g00680 | TCT | TTT | S | F |
| chr1 | − | − | − | − | − | + | − | − | − | T | A | Pp01g01360 | ATC | TTC | I | F |
| chr1 | − | − | − | − | − | − | + | − | − | C | T | Pp01g01670 | GGA | AGA | G | R |
| chr1 | − | − | − | − | − | − | + | − | − | A | G | Pp01g05180 | TTT | TCT | F | S |
| chr1 | − | − | − | − | − | − | + | − | − | T | C | Pp01g06840 | CTA | CCA | L | P |
| chr1 | − | − | − | + | − | − | − | − | − | A | G | Pp01g15120 | TCA | CCA | S | P |
| chr1 | + | − | − | − | − | − | − | − | − | C | T | Pp01g15160 | CCA | CTA | P | L |
| chr2 | + | − | − | − | − | − | − | − | − | T | A | Pp02g02120 | TTA | TAA | L | Stop |
| chr2 | − | + | − | − | − | − | − | − | − | C | T | Pp02g02120 | CAG | TAG | Q | Stop |
| chr2 | − | − | + | − | − | − | − | − | − | T | G | Pp02g02120 | TTA | TGA | L | Stop |
| chr2 | − | − | − | + | − | − | − | − | − | C | A | Pp02g02120 | TCG | TAG | S | Stop |
| chr2 | − | − | − | − | + | − | − | − | − | A | G | Pp02g02120 | GAA | GGA | E | G |
| chr2 | − | − | − | − | − | + | − | − | − | T | C | Pp02g02120 | TTC | TCC | F | S |
| chr2 | − | − | − | − | − | − | + | − | − | T | C | Pp02g02120 | TTC | CTC | F | L |
| chr2 | − | − | − | − | − | − | − | + | − | G | T | Pp02g02120 | TGC | TTC | C | F |
| chr2 | − | − | − | − | − | − | − | − | + | A | C | Pp02g02120 | AAA | AAC | K | N |
| chr2 | − | + | − | − | − | − | − | − | − | A | G | Pp02g02230 | AAT | GAT | N | D |
| chr2 | − | + | − | − | − | − | − | − | − | A | G | Pp02g02590 | TTG | TCG | L | S |
| chr2 | − | − | − | − | − | − | − | − | − | A | G | Pp02g07430 | ATT | CTT | I | L |
| chr2 | − | − | − | − | − | + | − | − | − | T | C | Pp02g08680 | GAA | GCA | E | A |
| chr2 | + | − | − | − | − | − | − | − | − | A | G | Pp02g08890 | TAC | TCC | Y | S |
| chr2 | − | − | − | − | − | − | + | − | − | C | T | Pp02g10380 | CAG | AAC | Q | N |
| chr3 | − | − | − | − | + | − | − | − | − | A | T | Pp03g00790 | AAA | TAA | K | Stop |
| chr3 | − | − | − | − | − | − | − | − | − | C | T | Pp03g03230 | CCA | TCA | P | S |
| chr3 | − | − | − | − | + | − | − | − | − | C | T | Pp03g03550 | TCT | TTT | S | F |
| chr3 | − | − | − | − | − | + | − | − | − | A | G | Pp03g03680 | ACC | AGC | T | S |
| chr3 | − | − | − | − | + | − | − | − | − | A | G | Pp03g08800 | TAT | CAT | Y | H |
| chr3 | + | − | − | − | − | − | − | − | − | A | G | Pp03g11050 | AAT | CAT | N | H |
| chr4 | + | − | − | − | − | − | − | − | − | T | C | Pp05g03460 | CAA | CGA | Q | R |
| chr4 | − | − | − | − | − | + | − | − | − | T | C | Pp05g04590 | AAA | GAA | K | E |
| chr4 | + | − | − | − | − | − | − | − | − | C | T | Pp05g04720 | CCC | CTC | P | L |
| chr4 | + | − | − | − | − | − | − | − | − | A | T | Pp05g06510 | TAT | TAA | Y | Stop |
| chr4 | − | − | − | − | + | − | − | − | − | A | G | Pp05g07960 | CTA | CCA | L | P |

FIG.4

CRZ1 MUTANT FUNGAL CELLS

This Application is a continuation of U.S. application Ser. No. 14/437,405, filed Apr. 21, 2015, now abandoned, which is the national phase filed International Application No. PCT/US2013/065443, filed Oct. 17, 2013 filed under 35 U.S.C. § 371 which claims the benefit of U.S. Provisional Patent Application No. 61/716,670, filed Oct. 22, 2012; each of which is herein incorporated by reference in its entirety.

FIELD OF THE INVENTION

The present invention relates to CRZ1 mutant allele and fungal host cells, such as *Pichia pastoris*, comprising such an allele along with methods of use thereof.

BACKGROUND OF THE INVENTION

GlycoFi has engineered *Pichia* to produce recombinant glycoproteins with human-like glycosylation. However, the extensive genetic modifications have also caused fundamental changes in cell wall structures, predisposing these glycoengineered strains to cell lysis and reduced cell robustness during fermentation. These undesirable traits have resulted in substantial reductions in cell viability as well as a marked increase in intracellular protease leakage into the fermentation broth, resulting in a reduction in both recombinant product yield and quality. Isolated fungal host cells, such as *Candida albicans, Hansenula polymorpha; Schizosaccharomyces pombe; Saccharomyces cerevisiae; Pichia pastoris*, lacking functional OCH1, a polypeptide in the fungal glycosylation pathway, are known to be temperature sensitive. For example, *Candida albicans* och1 knock-outs are temperature sensitive at 42° C. (Bates et al., Outer Chain N-Glycans Are Required for Cell Wall Integrity and Virulence of *Candida albicans*, The Journal of Biological Chemistry 281: 90-98 (2006); *Hansenula polymorpha* och1 knock-outs are temperature sensitive at 45° C. (Kim et al., Functional Characterization of the *Hansenula polymorpha* HOC1, OCH1, and OCR1 Genes as Members of the Yeast OCH1 Mannosyltransferase Family Involved in Protein Glycosylation, The Journal of Biological Chemistry, 281: 6261-6272 (2006)); *Schizosaccharomyces pombe* och1 knock-outs are temperature sensitive at 37° C. (Yoko-o et al., *Schizosaccharomyces pombe* och1+ encodes alpha-1,6-mannosyltransferase that is involved in outer chain elongation of N-linked oligosaccharides, FEBS Letters 489: 75-80 (2001)); *Saccharomyces cerevisiae* och1 knock-outs are temperature sensitive at 37° C. (Nakayama et al., OCH1 encodes a novel membrane bound mannosyltransferase: outer chain elongation of asparagine-linked oligosaccharides, EMBO J. 11(7):2511-9 (1992)); and *Pichia pastoris* och1 knock-outs are temperature sensitive at 37° C. (Choi et al., Use of combinatorial genetic libraries to humanize N-linked glycosylation in the yeast *Pichia pastoris*, Proc Natl Acad Sci USA. 100(9):5022-7 (2003)). Additional genetic modifications to make och1⁻ fungal host cells (e.g., *Pichia* cells) more robust in cell culture would be of value.

An unlikely candidate for genetic modification in order to increase *Pichia* culture robustness is CRZ1, a zinc finger transcription factor. CRZ1 is known to regulate a number of *S. cerevisiae* plasma membrane and cell wall regulatory genes (Cyert, Biochemical and Biophysical Research Communications 311:1143-1150 (2003)). Perturbation of plasma membrane and cell wall synthesis, due to mutation of CRZ1, would have been expected to make *Pichia* cells less robust. The published characterizations of *S. cervisiae* CRZ1 would have led a practitioner of ordinary skill in the art to predict that *Pichia* cells, lacking functional CRZ1, would be less viable and robust when placed under high temperature stress. (Matheos et al., Genes & Development 11:3445-3458 (1997); Stathopoulos et al., Genes & Development 11: 3432-3444 (1997)).

SUMMARY OF THE INVENTION

The present invention provides an isolated fungal host cell (e.g., *Pichia* such as *Pichia pastoris*) lacking functional CRZ1 polypeptide, e.g., wherein the cell exhibits increased fermentation robustness and production of heterologous polypeptides, such as immunoglobulins, relative to a cell expressing functional CRZ1, e.g., wherein endogenous CRZ1 has been mutated, disrupted or partially or fully deleted; optionally comprising a heterologous polynucleotide (e.g., operably linked to a promoter such as a methanol inducible promoter) that encodes a heterologous polypeptide such as an immunoglobulin. In an embodiment of the invention, (i) endogenous CRZ1 encodes a polypeptide that comprises one or more mutations selected from the group consisting of: L33-STOP; Q214-STOP; L294→STOP; S298→STOP; E403→G; F406→S; F406→L: C411→G; and K469→G; disruption of endogenous CRZ1, complete endogenous CRZ1 deletion, partial endogenous CRZ1 deletion (e.g., that deletes 33aa-end, 214aa-end, 294-end, 298-end of the CRZ1 polypeptide); or (ii) endogenous CRZ1 comprises one or more mutations selected from the group consisting of: a1407c; g1232t; t1216c; t1217c; a1208g; c893a; t881g; c640t; and t98a; or (iii) endogenous CRZ1 does not encode a functional C-terminal zinc-finger domain. In an embodiment of the invention, the isolated fungal host cell also comprises one or more (e.g., any 1, 2, 3, 4, 5, 6, 7, 8, 9, 10, 11, 12, 13 or 14) of the following characteristics: (i) wherein one or more endogenous beta-mannosyltransferase genes are mutated, disrupted, truncated or partially or fully deleted; (ii) comprising a polynucleotide encoding an alpha-1,2 mannosidase, an alpha-1,3 mannosidase, or an alpha-1,6 mannosidase; (iii) wherein one or more endogenous phosphomannosyl transferases are mutated, disrupted, truncated or partially or fully deleted; (iv) comprising a single-subunit oligosaccharyltransferase (e.g. *Leishmania* sp. STT3D); (v) wherein an endogenous dolichol-P-Man dependent alpha-1, 3-mannosyltransferase (e.g., ALG3) is mutated, disrupted, truncated or partially or fully deleted; (vi) comprising a polynucleotide encoding an endomannosidase; (vii) comprising one or more polynucleotides encoding a bifunctional UDP-N-acetylglucosamine-2-epimerase/N-acetylmannosamine kinase, an N-acetylneuraminate-9-phosphate synthase, or a CMP-sialic acid synthase; (viii) wherein an endogenous ATT1 gene is mutated, disrupted, truncated or partially or fully deleted; (ix) wherein an alpha-1,6-mannosyltransferase (e.g., OCH1) is mutated, disrupted, truncated or partially or fully deleted; (x) comprises a galactosyltransferase e.g., an alpha 1, 3-galactosyltransferase or a beta 1,4-galactosyltransferase; (xi) comprises a nucleotide sugar transporter, e.g., UDP-Galactose transporter (DmUGT); (xii) comprises a sialyltransferase, e.g., alpha-2,6-sialyl transferase (MmST6-33); (xiii) comprises a acetylglucosaminyl transferase, e.g., GNT1 or GNT2 or GNT4; and/or (xiv) wherein one or more endogenous protease genes (e.g., PEP4 and PRB1) are mutated, disrupted, truncated or partially or fully deleted. The present invention also provides a method for making the isolated fungal host cell of the present invention comprising introducing a heterologous polynucleotide into the cell which homologously recombines with the endogenous CRZ1 and partially or fully deletes the endogenous CRZ1 or disrupts the endogenous CRZ1, along with an isolated fungal host cell produced by such a method.

The present invention also provides an isolated polynucleotide which encodes a polypeptide comprising the amino acid sequence set forth in SEQ ID NO: 3 which comprises a mutation selected from the group consisting of: L33→STOP; Q214→STOP; L294→STOP; S298→STOP; E403→G, F406→S, F406→L, C411→F; and K469→N, e.g., comprising a nucleotide sequence of SEQ ID NO: 2 comprising a mutation selected from the group consisting of: a1407c; g1232t; t1216c; t1217c; a1208g; c893a; t881g; c640t; and t98a. Isolated vectors comprising such polynucleotides also form part of the present invention. Isolated polypeptides encoded by such polynucleotides are also part of the present invention.

The present invention also provides a method for producing an isolated crz1$^{mutant}$ fungal host cell (e.g., *Pichia* such as *Pichia pastoris*) having improved viability at high temperature (e.g., 32° C.) comprising introducing a mutation that encodes a polypeptide selected from the group consisting of: L33-STOP; Q214-STOP; L294-STOP; S298-STOP; E403→G; F406→S; F406→L; C411→F; and K469N; into the endogenous CRZ1 gene in the fungal cell.

The present invention also provides a method for producing one or more heterologous polypeptides (e.g., an immunoglobulin polypeptide) comprising: (i) introducing a polynucleotide encoding the heterologous polypeptide(s) into such an isolated cry1$^{mutant}$ fungal host cell (e.g., *Pichia* such as *Pichia pastoris*) (e.g., any of those discussed herein); and (ii) culturing the host cell under conditions favorable to expression of the heterologous polypeptide(s) in the cell (e.g., at 24° C.) and, optionally, (iii) isolating the heterologous polypeptide(s) from the host cell. In an embodiment of the invention, the heterologous polynucleotide that encodes the heterologous polypeptide is operably linked to a methanol inducible promoter and wherein the isolated fungal host cell is cultured under conditions favorable to expression of the heterologous polypeptide in the presence of methanol.

BRIEF DESCRIPTION OF THE FIGURES

FIG. 4: Deep sequencing of temperature-resistant mutants identified multiple mutations in Pp02g02120 (CRZ1) and two mutations in Pp01g00680 (ATT1), corresponds to circled "+" symbols.

DETAILED DESCRIPTION OF THE INVENTION

Figure 1:
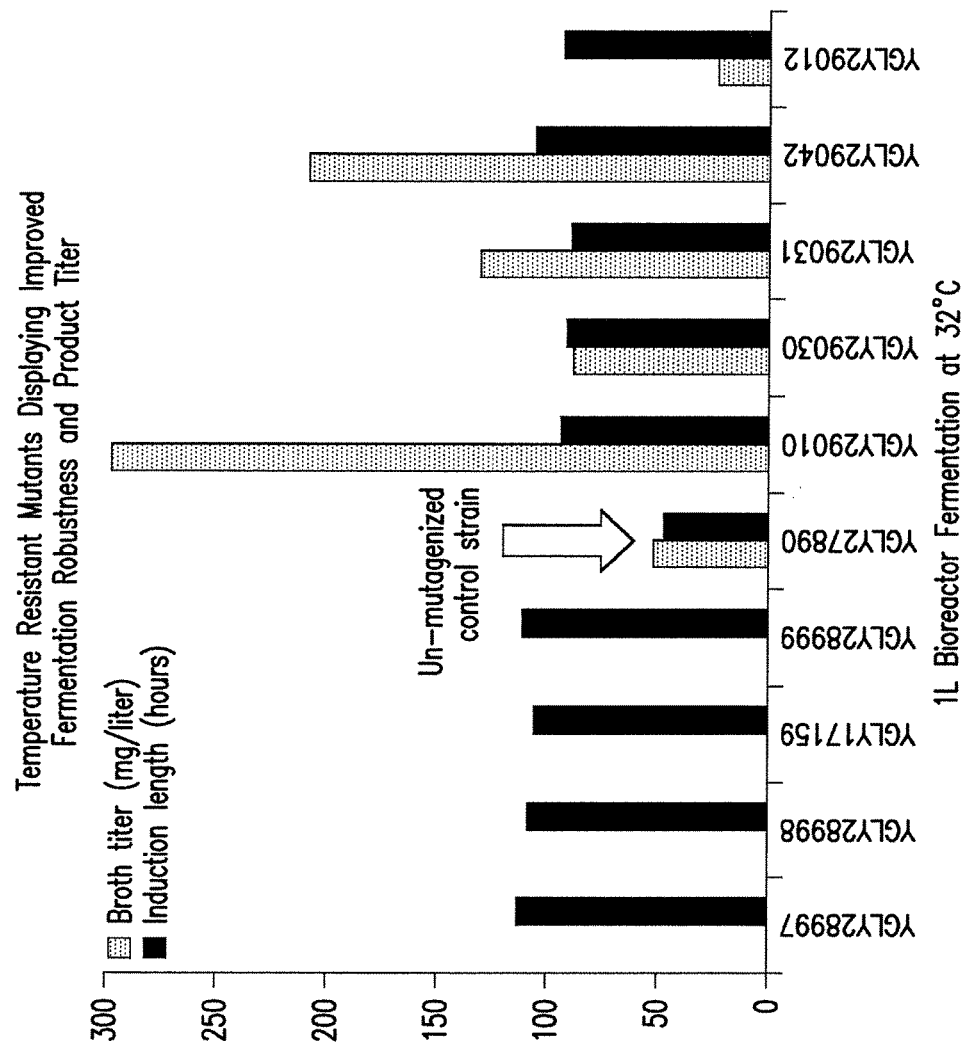
FIG. 1: Temperature resistant mutants displaying improved fermentation robustness and Fc titer.

Contrary to what was expected, *Pichia pastoris* cells, lacking functional CRZ1, exhibited enhanced temperature-resistance and increased robustness.

To broadly improve strain quality, random mutagenesis was conducted and several temperature-resistant mutant *Pichia pastoris* strains with significantly improved fermentation robustness were identified. Whereas the non-mutagenized glycoengineered parental strains display a temperature-sensitive phenotype (Choi et al. 2003) and are viable for 40 to 60 hours after induction at 32° C., the mutants all lasted between 90 to 110 hours after induction at 32° C. This extended induction period significantly increased the yield and quality of recombinant proteins expressed from these temperature-resistant strains. To uncover the mutations responsible for this increased thermal tolerance and fermentation robustness, genome-sequencing for 9 independently isolated mutants was performed, and non-synonymous mutations within distinct open reading frames (ORF) per mutant were identified. Remarkably, all 9 mutants contained distinct mutations within the coding region of one gene, *Pichia pastoris* CRZ1. More importantly, the *Pichia pastoris* CRZ1 mutation was the only non-synonymous single-nucleotide-variation (SNV) detected in three mutants YGLY29010, YGL29031, and YGL29042. Collectively, these genome-sequencing results show that the mutations within the *Pichia pastoris* CRZ1 gene were responsible for the temperature-resistance and fermentation robustness phenotypes. Moreover, non-mutagenized glyco-engineered strains in which endogenous CRZ1 was mutated, and, thus, lacked functional CRZ1 protein, similarly exhibited viability for 90-110 hours after induction at 32° C.

A "CRZ1$^{wt}$" fungal host cell comprises a wild-type CRZ1.

"PpCRZ1" is *Pichia pastoris* CRZ1.

"ScCRZ1" is *Saccharomyces cerevisiae* CRZ1.

High temperature with respect to the growth of isolated fungal cells such as *Pichia*, e.g., *Pichia pastoris*, is above 28° C., 29° C. or 30° C., e.g., 32° C.

A heterologous polynucleotide is a polynucleotide that has been introduced into a fungal host cell and that encodes a heterologous polypeptide. For example, a heterologous polynucleotide can encode an immunoglobulin heavy chain or an immunoglobulin light chain, e.g., comprising the light or heavy chain variable domain and, optionally, the antibody constant domain, e.g., from an antibody or antigen-binding fragment thereof, e.g., from a fully human antibody, humanized antibody, chimeric antibody, a bispecific antibody, an antigen-binding fragment of an antibody such as a Fab antibody fragment, F(ab)$_2$ antibody fragment, Fv antibody fragment, single chain Fv antibody fragment or a dsFv antibody fragment. Any such antibody can bind specifically to any epitope such as insulin-like growth factor 1 receptor, VEGF, interleukin-6 (IL6), IL6 receptor, respiratory syncitial virus (RSV), CD20, tumor necrosis factor alpha, receptor activated NF kappa B ligand (RANKL), or the RANKL receptor RANK, IgE, Her2, Her3, or the Epidermal growth factor receptor.

An "endogenous" gene is a chromosomal copy of the gene.

A glossary of gene names that may be mentioned herein is as follows:

| | | |
|---|---|---|
| ScSUC2 | S. cerevisiae Invertase | |
| OCH1 | Alpha-1,6-mannosyltransferase | |
| KlMNN2-2 | K. lactis UDP-GlcNAc transporter | nucleotide sugar transporter |
| BMT1 | Beta-mannose-transfer (beta-mannose elimination) | beta-mannosyltransferase |
| BMT2 | Beta-mannose-transfer (beta-mannose elimination) | |
| BMT3 | Beta-mannose-transfer (beta-mannose elimination) | |
| BMT4 | Beta-mannose-transfer (beta-mannose elimination) | |
| MNN4L1 | MNN4-like 1 (charge elimination) | |
| MmSLC35A3 | Mouse homologue of UDP-GlcNAc transporter | |
| PNO1 | Phosphomannosylation of N-linked oligosaccharides (charge elimination) | |
| MNN4 | Mannosyltransferase (charge elimination) | |
| ScGAL10 | UDP-glucose 4-epimerase | |
| XB33 | Truncated HsGalT1 fused to ScKRE2 leader | |
| DmUGT | UDP-Galactose transporter | |
| KD53 | Truncated DmMNSII fused to ScMNN2 leader | |
| TC54 | Truncated RnGNTII fused to ScMNN2 leader | |
| NA10 | Truncated HsGNTI fused to PpSEC12 leader | |
| FB8: | Truncated MmMNS1A fused to ScSEC12 leader | |
| MmCST | Mouse CMP-sialic acid transporter | |
| HsGNE | Human UDP-GlcNAc 2-epimerase/N-acetylmannosamine kinase | |
| HsCSS | Human CMP-sialic acid synthase | |
| HsSPS | Human N-acetylneuraminate-9-phosphate synthase | |
| MmST6-33 | Truncated Mouse alpha-2,6-sialyl transferase fused to ScKRE2 leader | |
| TrMDS1 | Secreted T. reseei MNS1 | |
| STE13 | Golgi dipeptidyl aminopeptidase | |
| DAP2 | Vacuolar dipeptidyl aminopeptidase | |
| ALG3 | dolichol-P-Man dependent alpha(1-3) mannosyltransferase | |
| STT3D | oligosaccharyltransferase | |
| CiMNS1 | Coccidioides immitis mannosidase I | |

Molecular Biology

In accordance with the present invention there may be employed conventional molecular biology, microbiology, and recombinant DNA techniques within the skill of the art. Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., James M. Cregg (Editor), Pichia Protocols (Methods in Molecular Biology), Humana Press (2010), Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999), Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" or "nucleic acid" includes DNA and RNA in single stranded form, double-stranded form or otherwise.

A "polynucleotide sequence" or "nucleotide sequence" is a series of nucleotide bases (also called "nucleotides") in a nucleic acid, such as DNA or RNA, and means a series of two or more nucleotides. Any polynucleotide comprising a nucleotide sequence set forth herein (e.g., crz1$^{mutant}$) forms part of the present invention.

A "coding sequence" or a sequence "encoding" an expression product, such as an RNA or polypeptide is a nucleotide sequence (e.g., heterologous polynucleotide) that, when expressed, results in production of the product (e.g., a heterologous polypeptide such as an immunoglobulin heavy chain and/or light chain).

As used herein, the term "oligonucleotide" refers to a nucleic acid, generally of no more than about 100 nucleotides (e.g., 30, 40, 50, 60, 70, 80, or 90), that may be hybridizable to a polynucleotide molecule. Oligonucleotides can be labeled, e.g., by incorporation of $^{32}$P-nucleotides, $^{3}$H-nucleotides, $^{14}$C-nucleotides, $^{35}$S-nucleotides or nucleotides to which a label, such as biotin, has been covalently conjugated.

A "protein", "peptide" or "polypeptide" (e.g., a heterologous polypeptide such as an immunoglobulin heavy chain and/or light chain) includes a contiguous string of two or more amino acids. Any polypeptide comprising an amino acid sequence set forth herein (e.g., Crz1$^{mutant}$ polypeptide) forms part of the present invention.

A "protein sequence", "peptide sequence" or "polypeptide sequence" or "amino acid sequence" refers to a series of two or more amino acids in a protein, peptide or polypeptide. The term "isolated polynucleotide" or "isolated polypeptide" includes a polynucleotide or polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences. The scope of the present invention includes the isolated polynucleotides set forth herein (e.g., crz1$^{mutant}$) and isolated polypeptides encoded by such polynucleotides.

An isolated polynucleotide or polypeptide will, preferably, be an essentially homogeneous composition of molecules but may contain some heterogeneity.

"Amplification" of DNA as used includes the use of polymerase chain reaction (PCR) to increase the concentration of a particular DNA sequence within a mixture of DNA sequences. For a description of PCR see Saiki, et al., Science (1988) 239:487.

In general, a "promoter" or "promoter sequence" is a DNA regulatory region capable of binding an RNA polymerase in a cell (e.g., directly or through other promoter-bound proteins or substances) and initiating transcription of a coding sequence to which it operably links. Crz1$^{mutant}$ polynucleotide operably linked to a promoter forms part of the present invention. Also, an isolated crz1$^{mutant}$ fungal host cell comprising a heterologous polynucleotide (e.g., encoding an immunoglobulin polypeptide) operably linked to a promoter also forms part of the present invention.

A coding sequence (e.g., of a heterologous polynucleotide, e.g., reporter gene or immunoglobulin heavy and/or light chain) is "operably linked to", "under the control of", "functionally associated with" or "operably associated with" a transcriptional and translational control sequence (e.g., a promoter of the present invention) when the sequence directs RNA polymerase mediated transcription of the coding sequence into RNA, preferably mRNA, which then may be RNA spliced (if it contains introns) and, optionally, translated into a protein encoded by the coding sequence.

The present invention includes vectors or cassettes which comprise crz1$^{mutant}$ polynucleotide. Vectors containing a heterologous polynucleotide encoding a heterologous polypeptide can also be used in various crz1$^{mutant}$ fungal host cells for production of the heterologous polypeptide (e.g., an immunoglobulin). The term "vector" includes a vehicle (e.g., a plasmid) by which a DNA or RNA sequence can be introduced into a host cell, so as to transform the host and, optionally, promote expression and/or replication of the introduced sequence. Suitable vectors for use herein include plasmids, integratable DNA fragments, and other vehicles that may facilitate introduction of the nucleic acids into the genome of a host cell (e.g., *Pichia pastoris*). Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass. Such vectors optionally include a secretion signal (e.g., alpha-mating factor (α-MF) pre-pro leader sequence) operably linked to a heterologous polynucleotide. Also, an isolated crz1$^{mutant}$ fungal host cell comprising a vector that includes a heterologous polynucleotide (e.g., encoding an immunoglobulin polypeptide), e.g., operably linked to a promoter, also forms part of the present invention.

A polynucleotide (e.g., a heterologous polynucleotide, e.g., encoding an immunoglobulin heavy chain and/or light chain), operably linked to a promoter, may be expressed in an expression system. The term "expression system" means a host cell and compatible vector which, under suitable conditions, can express a protein or nucleic acid which is carried by the vector and introduced to the host cell. Common expression systems include fungal host cells (e.g., *Pichia pastoris*) and plasmid vectors, insect host cells and Baculovirus vectors, and mammalian host cells and vectors.

The term methanol-induction refers to increasing expression of a polynucleotide (e.g., a heterologous polynucleotide) operably linked to a methanol-inducible promoter in a host cell of the present invention by exposing the host cells to methanol. A cry1$^{mutant}$ containing a polynucleotide operably linked to a methanol-inducible promoter forms part of the present invention. Methods for inducing expression of a heterologous polynucleotide fused to such a methanol-inducible promoter by exposing a crz1$^{mutant}$ fungal cell comprising the promoter construct to methanol, and culturing the cell under conditions favorable to expression of the encoded heterologous polypeptide form part of the present invention.

The following references regarding the BLAST algorithm are herein incorporated by reference: BLAST ALGORITHMS: Altschul, S. F., et al., J. Mol. Biol. (1990) 215: 403-410; Gish, W., et al., Nature Genet. (1993) 3:266-272; Madden, T. L., et al., Meth. Enzymol. (1996) 266:131-141; Altschul, S. F., et al., Nucleic Acids Res. (1997) 25:3389-3402; Zhang, J., et al., Genome Res. (1997) 7:649-656; Wootton, J. C., et al., Comput. Chem. (1993) 17:149-163; Hancock, J. M., et al., Comput. Appl. Biosci. (1994) 10:67-70; ALIGNMENT SCORING SYSTEMS: Dayhoff, M. O., et al., "A model of evolutionary change in proteins." in *Atlas of Protein Sequence and Structure*, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., J. Mol. Biol. (1991) 219:555-565; States, D. J., et al., Methods (1991) 3:66-70; Henikoff, S., et al., Proc. Natl. Acad. Sci. USA (1992)89: 10915-10919; Altschul, S. F., et al., J. Mol. Evol. (1993) 36:290-300; ALIGNMENT STATISTICS: Karlin, S., et al., Proc. Natl. Acad. Sci. USA (1990) 87:2264-2268; Karlin, S., et al., Proc. Natl. Acad. Sci. USA (1993) 90:5873-5877; Dembo, A., et al., Ann. Prob. (1994) 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

CRZ1

The present invention comprises isolated CRZ1 polynucleotides comprising a mutation (crz1$^{mutant}$ polynucleotides) and polypeptides encoded by such polynucleotides (crz1$^{mutant}$ polypeptides) along with isolated fungal host cells comprising endogenous CRZ1 that has been mutated in such a way (e.g., by mutation, partial or complete deletion, or disruption). Specific examples of such mutations in the *Pichia pastoris* CRZ1 polynucleotide are polynucleotides comprising the nucleotide sequence of SEQ ID NO: 2 having one or more of the following mutations: a1407c;

g1232t; t1216c; t1217c; a1208g; c893a; t881 g; c640t; and t98a. These CRZ1 polynucleotides encode CRZ1 polypeptides having the amino acid sequence of SEQ ID NO: 3 having one or more of the following mutations: L33-STOP; Q214-STOP; L294→STOP; S298→STOP; E403→G; F406→S; F406→L; C411→F; and K469→N. Such mutant polynucleotides can be introduced into the endogenous CRZ1 chromosomal locus to replace the wild-type, endogenous CRZ1 with the mutated CRZ1.

The present invention encompasses any CRZ1 polynucleotide comprising a mutation that encodes a CRZ1 polypeptide lacking a functional C-terminal zinc-finger domain (e.g., a non-sense mutation or deletion that truncates the zinc-finger domain). Such polypeptides are also within the scope of the present invention.

The zinc-finger domain of *Pichia pastoris* CRZ1 polypeptide comprises the amino acid sequence: SIYACSLCSKRFTRPYNLKSHLRTHADERPFQCSICGKAFARSHDRKR HEDLHSGERKYCCKGVLSDGVTTWGCEKRFARTDALGRHFKTECGKLC (amino acids 376-471 of SEQ ID NO: 3).

A BLASTP comparison between *Saccharomyces cerevisiae* CRZ1 polypeptide (SEQ ID NO: 1) and *Pichia pastoris* CRZ1 polypeptide (SEQ ID NO: 3) identified in the random mutatgenesis screen is as follows:

```
                    1                                                  50
ScCRZ1   (1) MSFSNGNMASYMTSSNGEEQSINNKNDIDDNSAYRRNNFRNSSNSGSHTF
PpCRZ1   (1) ----------------MADQRLEDEFDISRYLSISP--------------

51                                                 100
ScCRZ1  (51) QLSDLDLDVDMRMDSANSSEKISKNLSSGIPDSFDSNVNSLLSPSSGSYS
PpCRZ1  (21) ------------IESASIEESINGLMSSWIPPAKGEIRDSLP-PNASFEA 101                                                 150
ScCRZ1 (101) ADLNYQSLYKPDLPQQQLQQQQLQQQQQQQQQQQQQQKQTPTLKVEQSD
PpCRZ1  (58) TDSFSTSSYQEIIPAQVKIKLEFDNDQQPVFYQESQ--P-----------

151                                                 200
ScCRZ1 (151) TFQWDDILTPADNQHRPSLTNQFLSPRSNYDGTTRS-SGIDSNYSDTESN
PpCRZ1  (95) --VYDKHLTVNDQETR---SAQDFNQYLNADAVSRTNSISNLSELSTHSH 201                                                 250
ScCRZ1 (200) YHTPYLYPQDLVSSPAMSHLTANNDDFDDLLSVASMNSNYLLPVNSHGYK
PpCRZ1 (140) ITPPTLLHDQASLSPALLSMNSDERNELNLETLQLDQTSQPYVNQIKTEA 251                                                 300
ScCRZ1 (250) HISNLDELDDLLSLTYSDNNLLSASNNSDFNNSNNGIINTADTQNSTIAI
PpCRZ1 (190) AYEELSELHHRLERLTETNLIHQDQLQLEQQEQQN-------------QT 301                                                 350
ScCRZ1 (300) NKSKVGTNQKMLLTIPTSSTPSPSTHAAPVTPIISIQEFNEGHFPVKNED
PpCRZ1 (227) PHT---LSPPIQLQTPIIKVLQAPNDIAANTPSLFSQSNHSSPYNTPKHS 351                                                 400
ScCRZ1 (350) DGTLQLKVRDNESYSATNNNNLLRPDDNDYNNEALSDIDRSFEDIINGRK
PpCRZ1 (274) R----------------S-NSLSSNDRQHDIPQISSVLDTSSFLVPGDQ
                                                              ^     ^

401                                                 450
ScCRZ1 (400) LKLKKSRRRSSQTSNNSFTSRRSSRSRSISPDEKAKSISANREKLLEMAD
PpCRZ1 (306) FQAMREGRQRRKSESNSRNSKERSKSR-----EPPKSRSRSR--------

451                                                 500
ScCRZ1 (450) LLPSSENDNNRERYDNDSKTSYNTINSSNFNEDNNNNNLLTSKPKIESGI
PpCRZ1 (343) ---------------DSATDHHMEVMS----REKTLELAASQP------

501                                                 550
ScCRZ1 (500) VNIKNELDDTSKDLGILLDIDSLGQFEQKVGFKNDDNHENNDNGTFSVKK
PpCRZ1 (367) -----------------------------------------------S-

551                                                 600
ScCRZ1 (550) NDNLEKLDSVTNNRKNPANFACDVCGKKFTRPYNLKSHLRTHTNERPFIC
PpCRZ1 (368) SK--TPQ-------KNPSIYACSLCSKRFTRPYNLKSHLRTHADERPFQC
                                                              *    *

601                                                 650
ScCRZ1 (600) SICGKAFARQHDRKRHEDLHTGKKRYVCGGKLKDGKP-WGCKKFARSDA
PpCRZ1 (409) SICGKAFARSHDRKRHEDLHSGERKYCCKGVLSDGVTTWGCEKRFARTDA
                      *

651                                                 700
ScCRZ1 (649) LGRHFKTESGRRCITPLYEEARQEKSGQES-------------------
PpCRZ1 (459) LGRHFKTECGKLCIKPLMDELKREEAYRRNEPVTEMNDELYSQSVQDIFS
                      *
```

```
                701
ScCRZ1 (679) ----------
PpCRZ1 (509) SQRLGQNIDD
```

The present invention comprises mutant *Pichia pastoris* and *Saccharomyces cerevisiae* CRZ1 polypeptides and polynucleotides encoding such polypeptides. Specific examples of *Pichia pastoris* and *Saccharomyces cerevisiae* CRZ1 polypeptides comprise one or more changes to the amino acid sequence set forth in SEQ ID NO: 1 at the locations noted with a * or ˆ in the BLASTP comparison shown above The identity of CRZ1 is known in the art. Specific examples of CRZ1 are set forth below. In an embodiment of the invention, *Saccharomyces cerevisiae* or *Pichia pastoris* CRZ1 polypeptide comprises at least about 90% (e.g., 90%, 91%, 92%, 93%, 94%, 95%, 96%, 97%, 98%, or 99%) sequence similarity or identity to SEQ ID NO: 1 or 3, respectively. In an embodiment of the invention, *Pichia pastoris* CRZ1 polynucleotide comprises at least about 90% (e.g., 90%, 91%, 92%, 93%, 94%, 95%, 96%, 97%, 98%, or 99%) sequence identity to SEQ ID NO: 2.

```
Saccharomyces cerevisiae CRZ1 wild-type
polypeptide
                                   (SEQ ID NO: 1)
msfsngnmas ymtssngeeq sinnkndidd nsayrrnnfr nssnsgshtf qlsdldldvd mrmdsansse kisknlssgi pdsfdsnvns llspssgsys adlnyqslyk pdlpqqqlqq qqqqqqqqqq qqqqqqkqtp tlkveqsdtf qwddiltpad nqhrpsltnq flsprsnydg ttrssgidsn ysdtesnyht pylypqdlvs spamshltan nddfddllsv asmnsnyllp vnshgykhis nldelddlls ltysdnnlls asnnsdfnns nngiintadt qnstiainks kvgtnqkmll tiptsstpsp sthaapvtpi isiqefnegh fpvkneddgt lqlkvrdnes ysatnnnnll rpddndynne alsdidrsfe diingrklkl kksrrrssqt snnsftsrrs srsrsispde kaksisanre kllemadllp ssendnnrer ydndsktsyn tinssnfned nnnnnlltsk pkiesgivni knelddtskd lgilldidsl gqfeqkvgfk nddnhenndn gtfsvkkndn lekldsvtnn rknpanfacd vcgkkftrpy nlkshlrtht nerpficsic gkafarqhdr krhedlhtgk kryvcggklk dgkpwgcgkk farsdalgrh fktesgrrci tplyeearqe ksgqes Pichia pastoris CRZ1 wild-type open reading
frame
                                   (SEQ ID NO: 2)
ATGGCAGACCAACGGCTTGAGGATGAGTTTGATATCTCCAGATACTTATC

TATTTCTCCTATCGAGTCAGCTTCAATCGAAGAATCAATCAACGGTTTAA

TGAGTAGTTGGATTCCTCCGGCTAAGGGTGAGATTAGAGATTCACTTCCT

CCAAACGCTTCTTTTGAAGCTACAGACAGTTTTTCAACCAGTTCATACCA

GGAAATTATACCAGCACAGGTGAAAATAAAACTGGAGTTTGATAATGACC

AGCAGCCTGTTTTCTATCTAGAATCGCAACCAGTTTATGATAAGCATTTA
```

```
                             -continued
ACCGTCAATGATCAGGAAACCAGAAGCGCCCAAGACTTCAACCAATACTT

GAATGCTGATGCCGTATCGAGGACCAACTCCATCTCCAACTTATCGGAGC

TGTCAACTCATTCCCATATTACCCCTCCAACGCTACTTCATGATCAAGCC

TCATTGTCTCCTGCTCTCTTATCTATGAACAGTGATGAAAGAAACGAACT

CAATCTGGAAACACTACAGCTAGATCAAACGTCACAGCCTTACGTGAATC

AGATAAAAACGGAGGCAGCTTACGAAGAGCTTTCAGAGTTACACCACAGA

TTAGAAAGACTCACTGAGACAAATTTAATTCATCAAGACCAGCTTCAACT

CGAACAACAAGAGCAACAAAATCAGACTCCTCATACTCTCAGTCCTCCTA

TACAACTTCAGACTCCCATAATCAAAGTCTTGCAAGCCCCAAATGATATA

GCAGCAAATACCCCGTCTCTTTTTCTCAATCTAACCATTCATCTCCATA

TAACACACCCAAACATTCCAGGTCAAACTCGTTGAGTTCAAATGACAGAC

AACATGATATTCCACAAATATCCTCAGTTTTAGACACGTCTTCGTTTTTG

GTACCTGGAGATCAGTTTCAAGCAATGAGAGAAGGTAGACAGAGGAGGAA

ATCCGAGTCCAACTCTAGAAACTCGAAAGAACGTTCTAAATCTAGGGAAC

CGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAG

CTCCAAGACGCCGCAAAAGAACCCTTCCATCTATGCTTGCTCGCTCTGCT

CCAAGAGATTCACAAGACCATATAATTTGAAGTCTCACCTTCGCACGCAC

GCTGATGAAAGGCCTTTCCAGTGTTCAATATGCGGGAAGGCATTTGCTCG

TTCTCACGACAGAAAGCGTCATGAGGATCTGCATAGTGGTGAACGAAAGT

ATTGCTGCAAAGGTGTTTTGTCTGACGGAGTAACTACATGGGGCTGTGAA

AAAAGATTTGCCCGAACAGATGCGCTGGGTAGACATTTCAAAACTGAATG

TGGTAAACTGTGTATCAAGCCGCTGATGGATGAACTAAAGAGGGAGGAAG

CTTACAGGAGGAATGAACCAGTAACAGAAATGAATGACGAGCTTTACTCC

CAATCTGTCCAAGATATATTTAGCTCTCAGCGGCTTGGTCAGAACATAGA

TGACtga

Pichia pastoris CRZ1 wild-type polypeptide
                                   (SEQ ID NO: 3)
MADQRLEDEFDISRYLSISPIESASIEESINGLMSSWIPPAKGEIRDSLP

PNASFEATDSFSTSSYQEIIPAQVKIKLEFDNDQQPVFYQESQPVYDKHL

TVNDQETRSAQDFNQYLNADAVSRTNSISNLSELSTHSHITPPTLLHDQA

SLSPALLSMNSDERNELNLETLQLDQTSQPYVNQIKTEAAYEELSELHHR

LERLTETNLIHQDQLQLEQQEQQNQTPHTLSPPIQLQTPIIKVLQAPNDI

AANTPSLFSQSNHSSPYNTPKHSRSNSLSSNDRQHDIPQISSVLDTSSFL

VPGDQFQAMREGRQRRKSESNSRNSKERSKSREPPKSRSRSRDSATDHHM

EVMSREKTLELAASQPSSKTPQKNPSIYACSLCSKRFTRPYNLKSHLRTH
```

-continued

ADERPFQCSICGKAFARSHDRKRHEDLHSGERKYCCKGVLSDGVTTWGCE

KRFARTDALGRHFKTECGKLCIKPLMDELKREEAYRRNEPVTEMNDELYS

QSVQDIFSSQRLGQNIDD*

Host Cells

The present invention includes isolated crz1$^{mutant}$ fungal host cells which may include additional mutations in its genetic background. In a "crz1$^{mutant}$" fungal host cell (haploid or diploid), the endogenous chromosomal CRZ1 genes have been mutated, disrupted or partially or fully deleted, or expression of CRZ1 protein has been reduced in any way (e.g., by anti-sense RNA, interfering RNA such as small interfering RNA (SiRNA)), or the activity of the CRZ1 polypeptide has been chemically inactivated (e.g., by small molecule inhibitors), and thus, the cell partially or fully lacks functional CRZ1 polypeptide levels and/or CRZ1 activity to any degree relative to an isolated fungal host cell wherein CRZ1 has not been mutated or interfered with or the like. In an embodiment of the invention, the crz1$^{mutant}$ fungal host cell is more viable (e.g., in a fermentor or bioreactor) at high temperature or at 24° C. than a fungal host cell comprising the full level of CRZ1, e.g., at 32° C., e.g., for up to about 90-110 hours of induction at 32° C. In an embodiment of the invention, an isolated crz1$^{mutant}$ fungal host cell (e.g., in a fermentor or bioreactor) comprising a heterologous polynucleotide, e.g., encoding an Fc polypeptide, expresses significantly more heterologous polypeptide (e.g., 4 times or 5 times more), e.g., Fc polypeptide, than a CRZ1 wild-type fungal host cell comprising such a heterologous polynucleotide encoding an Fc polypeptide (such crz1$^{mutant}$ fungal host cells are within the scope of the present invention). In an embodiment of the invention, an isolated crz1$^{mutant}$ fungal host cell (e.g., in a fermentor or bioreactor) comprising a heterologous polynucleotide, e.g., encoding a heterologous Fc polypeptide, express heterologous polypeptide, e.g., Fc polypeptide, with an N-glycan profile essentially identical to that of a CRZ1$^{wt}$ fungal host cell, e.g., are able to effectively modify their N-glycans, e.g., Fc N-glycans, with high levels of terminal sialic acids, and/or with A2 levels ranging from 77 to 84%, and/or A1 levels from 4 to 7% (such crz1$^{mutant}$ fungal host cells are within the scope of the present invention).

In an embodiment of the invention, the isolated crz1$^{mutant}$ fungal host cell of the present invention comprises endogenous mutant CRZ1 polypeptide, e.g., which comprises the amino acid sequence of SEQ ID NO: 3 having one or more of the following mutations: L33-STOP; Q214→STOP; L294→STOP; S298→STOP; E403→G; F406→S; F406→S; C411→F; and K469→N; e.g., in an embodiment of the invention, the mutant endogenous CRZ1 polynucleotide of the isolated crz1$^{mutant}$ fungal host cell comprises a nucleotide sequence of SEQ ID NO: 2 having one or more of the following mutations: a1407c, g1232t; t1216c; t1217c; a1208g, c893a; t881g; c640t; and t98a. In an embodiment of the invention, in an isolated crz1$^{mutant}$ fungal host cell of the present invention, endogenous CRZ1 is mutated such that it lacks a functional C-terminal zinc-finger domain, e.g., due to mutation or truncation. In an embodiment of the invention, the fungal host cell endogenous CRZ1 has been replaced with a mutant CRZ1, e.g., any of those set forth herein such as a partial deletion mutant, a complete deletion mutant or a mutant comprising a nonsense mutation.

An endogenous CRZ1 gene in an isolated cry1$^{mutant}$ fungal host cell may be partially deleted, thus leaving only part of the CRZ1 coding sequence in the chromosomal locus where CRZ1 would naturally occur (e.g., wherein the CRZ1 zinc finger domain is partially or fully deleted); fully deleted, thus leaving no CRZ1 coding sequence in the chromosomal locus wherein CRZ1 would naturally occur (e.g., wherein CRZ1 is fully deleted and replaced with another polynucleotide such as an auxotrophic marker); disrupted, thus inserting a heterologous sequence into the chromosomal CRZ1 gene; mutated at one or more points in the chromosomal gene; mutated so as to lower CRZ1 expression levels or activity in the cell (e.g., wherein a partially or fully inactivating mutation is introduced into the CRZ1 zinc finger domain) as compared to a cell wherein CRZ1 has not been so mutated; or otherwise inactivated partially or fully in any way whatsoever. Alternatively, the regulatory region of such an endogenous CRZ1 gene may be partially or fully deleted, disrupted or mutated such that no significant amount of functional CRZ1 polypeptide is expressed in the cell. Moreover, CRZ1 expression can be lowered or eliminated in any way, e.g., by interference with expression using anti-sense CRZ1 molecules, SiRNA CRZ1 molecules, or by enhancing CRZ1 protein degradation, or by chemical inhibition using small molecule inhibitors. Such isolated crz1$^{mutant}$ fungal host cells are part of the present invention.

The scope of the present invention encompasses isolated crz1$^{mutant}$ fungal host cells that are "viable" at high temperature, and are more robust during fermentation, as well as uses of such cells as discussed herein. Isolated fungal host cell viability in a liquid cell culture, within a bioreactor/fermentor environment, for example, at high temperature such as 32° C., is, in an embodiment of the invention, determined by measuring cellular lysis in the cell culture. crz1$^{mutant}$ fungal host cellular lysis is, in an embodiment of the invention, evaluated microscopically or by determining the double stranded DNA content of the culture medium. Microscopic evaluation is done to score the amount of cellular debris that is observed in the culture medium. Cellular debris in the culture medium is a result of cell lysis and, thus, a marker for cell lysis and a means by which to determine cell viability in the culture. A score of 1, 2, 3, 4 or 5 is given; with 5 representing the most lysis, i.e., greater than 90% cellular lysis. crz1$^{mutant}$ fungal host cells exhibited less than a 5 score for lysis for between 90 and 110 hours following induction at 32° C. The culture medium containing crz1$^{mutant}$ fungal host cells induced at 32° C. had 30 micrograms/milliliter or less double stranded DNA for between 90 and 110 hours. When the cells lyse, double stranded DNA is released into the medium; thus, double stranded DNA content of the culture is a marker for cell lysis and a means by which to determine cell viability in the culture. Double stranded DNA can be determined using any of several methods known in the art including by determining the amount of fluorescent dye, with an affinity for double stranded DNA (e.g., bisbenzimide, an indole-derived stain such as Hoechst 33342, Hoechst 33258 or 49,6-diamidino-2-phenylindole; a phenanthridinium stain such as ethidium bromide or propidium Iodide; or a cyanine dye such as PicoGreen, YOYO-1 iodide, SYBR Green I or SYBR Gold; see, for example, Cosa et al., Photochemistry and Photobiology 73(6):585-599 (2001)), bound to double stranded DNA in the culture medium. The quantity of double stranded DNA in the culture can then be determined on this basis. Accordingly, cells in culture with a microscopic lysis score of less than 5 and/or a double stranded DNA content of 30 micrograms/milliliter or less are considered "viable".

Isolated fungal host cell viable for about 90 to about 110 hours after induction (e.g., in a bioreactor or fermentor) at 32° C. may be referred to herein as a "temperature-resistant" or "temperature-resistance" phenotype.

The present invention includes such host cells comprising a heterologous polynucleotide encoding a heterologous polypeptide (e.g., a reporter or immunoglobulin heavy and/or light chain) wherein the heterologous polynucleotide may be operably linked to a promoter; as well as methods of use thereof, e.g., methods for expressing the heterologous polypeptide in the fungal host cell. For example, the present invention includes methods for making one or more heterologous polypeptides in an isolated crz1$^{mutant}$ fungal host cell (e.g., *Pichia*) comprising, optionally, one or more further changes (e.g., mutations to endogenous genes and/or expression of one or more other genes; e.g., as discussed herein, for example, to produce modified glycosylation of expressed polypeptides) comprising (i) introducing a polynucleotide encoding the heterologous polypeptide into the crz1$^{mutant}$ fungal host cell and (ii) culturing the crz1$^{mutant}$ fungal host cell under conditions favorable to expression of the heterologous polypeptide in the cell and, optionally, (iii) isolating the heterologous polypeptide from the crz1$^{mutant}$ fungal host cell.

In an embodiment of the invention, a crz1$^{mutant}$ fungal host cell also comprises a mutation in ATT1. In one embodiment of the invention, a crz1$^{mutant}$ fungal host cell does not comprise a mutation in ATT1, e.g., endogenous ATT1 is wild-type, (e.g., the cell comprises wild-type, functional ATT1 polypeptide)-such cells and their uses, as discussed herein, are part of the present invention.

Isolated fungal host cells of the present invention are cells belonging to the Fungi kingdom, for example, in an embodiment of the invention, the fungal host cell is any yeast such as a budding yeast and/or a fission yeast. In an embodiment of the invention, the host cell is any methylotrophic yeast. Methylotrophic yeasts are a small group of yeast species capable of utilizing methanol as the sole source of carbon and energy. Examples of methylotrophic yeast include *Pichia pastoris*, *Pichia angusta* (*Hansenula polymorpha*), *Pichia methanolica*, and *Candida boidinii*. In an embodiment of the invention, the host cell is selected from the group consisting of any *Pichia* cell, such as *Pichia pastoris*, *Pichia angusta* (*Hansenula polymorpha*), *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis* or *Pichia methanolica*, *Saccharomyces cerevisiae*, *Saccharomyces* sp., *Hansenula polymorpha*, *Kluyveromyces* sp., *Kluyveromyces lactis*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum* and *Neurospora crassa*. In one particular embodiment of the invention, an isolated fungal host cell is as discussed above except that the term excludes *Saccharomyces cerevisiae*.

In an embodiment of the invention, the isolated fungal host cell is glycoengineered. In an embodiment of the invention, such a cell has been genetically engineered to produce glycoproteins where the N- or O-linked glycosylation are modified from their native form, e.g., either through inactivation or deletion of genes involved in N-glycosylation such as OCH1, ALG3, PNO1, and/or BMT1, BMT2, BMT3, BMT4, or genes involved in 0-glycosylation such as PMT1, PMT2 and/or PMT4 or though heterologous expression of glycosyltransferases such as GnTI, GnTII, GalT, and/or SialT, or glycosidases such as MNSI and/or MNSII. For example, in an embodiment of the invention, a glycoengineered isolated fungal host cell comprises any one or more of the following characteristics:

(i) wherein one or more endogenous beta-mannosyltransferase genes are mutated, disrupted, truncated or partially or fully deleted;

(ii) comprising a polynucleotide encoding an alpha-1,2 mannosidase enzyme;

(iii) wherein one or more endogenous phosphomannosyl transferases are mutated, disrupted, truncated or partially or fully deleted;

(iv) comprising a single-subunit oligosaccharyltransferase (e.g. *Leishmania* sp. STT3D);

(v) wherein an endogenous dolichol-P-Man dependent alpha-1,3-mannosyltransferase (e.g., Alg3) is mutated, disrupted, truncated or partially or fully deleted;

(vi) comprising a polynucleotide encoding an endomannosidase;

(vii) comprising one or more polynucleotides encoding a bifunctional UDP-N-acetylglucosamine-2-epimerase/N-acetylmannosamine kinase, an N-acetylneuraminate-9-phosphate synthase, or a CMP-sialic acid synthase;

(viii) wherein endogenous ATT1 gene is mutated, truncated or partially or fully deleted;

(ix) wherein an endogenous alpha-1,6-mannosyltransferase (e.g. OCH1) is mutated, disrupted, truncated or partially or fully deleted;

(x) comprising a polynucleotide encoding galactosyltransferase;

(xi) comprising a polynucleotide encoding nucleotide sugar transporter;

(xii) comprising a polynucleotide encoding sialyltransferase;

(xiii) comprising a polynucleotide encoding acetylglucosaminyl transferase and/or (xiv) wherein one or more endogenous proteases (e.g., PEP4 and PRB1) are mutated, disrupted, truncated or partially or fully deleted. Mutation of CRZ1 in glycoengineered isolated fungal host cells has been shown, herein, to reverse temperature sensitivity, to enhance cell robustness during fermentation, and to reverse poor production, i.e., to increase production, of heterologous polypeptides, such as immunoglobulins, at least in part, in such cells. Such glycoengineered isolated fungal host cells are part of the present invention. Methods for reversing temperature sensitivity and/or enhancing cell robustness during fermentation of a glycoengineered isolated fungal host cell by mutating CRZ1 or otherwise decreasing expression of CRZ1 polypeptide are also part of the present invention.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms." "PNGase", or "glycanase" refer to peptide N-glycosidase F (EC 3.2.2.18).

In an embodiment of the invention, an isolated $crz1^{mutant}$ fungal host cell, such as a Pichia cell (e.g., Pichia pastoris), is genetically engineered to include a nucleic acid that encodes an α-1,2-mannosidase that has a signal peptide that directs it for secretion. For example, in an embodiment of the invention, the $cry1^{mutant}$ host cell is engineered to express an exogenous α-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_5GlcNAc_2$. See U.S. Pat. No. 7,029,872. The present invention includes methods for producing one or more heterologous polypeptides comprising (i) introducing a polynucleotide encoding the heterologous polypeptide(s) into such a $crz1^{mutant}$, α-1,2-mannosidase$^+$ host cell and (ii) culturing the host cell under conditions favorable to expression of the heterologous polypeptide(s) in the cell and, optionally, (iii) isolating the heterologous polypeptide(s) from the host cell. The invention also encompasses a method for producing a heterologous recombinant glycoprotein comprising an N-glycan structure that comprises a $Man_5GlcNAc_2$ glycoform in a $cry1^{mutant}$ fungal host cell that does not display alpha-1,6 mannosyltransferase (e.g. OCH1) activity with respect to the N-glycan on a glycoprotein, the method comprising the step of introducing into the $crz1^{mutant}$ och1$^-$ fungal host cell, a polynucleotide encoding the heterologous recombinant glycoprotein, and a polynucleotide encoding an alpha-1,2 mannosidase enzyme selected to have optimal activity in the ER or Golgi of said host cell, the enzyme comprising: (a) an alpha-1,2 mannosidase catalytic domain having optimal activity in said ER or Golgi at a pH between 5.1 and 8.0; fused to (b) a cellular targeting signal peptide not normally associated with the catalytic domain selected to target the mannosidase enzyme to the ER or Golgi apparatus of the host cell; and culturing the fungal host cell under conditions favorable to expression of the heterologous recombinant glycoprotein, whereby, upon expression and passage of the heterologous recombinant glycoprotein through the ER or Golgi apparatus of the host cell, in excess of 30 mole % of the N-glycan structures attached thereto have a $Man_5GlcNAc_2$ glycoform that can serve as a substrate for GlcNAc transferase I in vivo.

Isolated $crz1^{mutant}$ fungal host cells of the present invention, such as Pichia host cells (e.g., Pichia pastoris) are, in an embodiment of the invention, genetically engineered to eliminate glycoproteins having alpha-mannosidase-resistant N-glycans by deleting or disrupting one or more of the β-mannosyltransferase genes (e.g., BMTI, BMT2, BMT3, and/or BMT4) (See, U.S. Pat. No. 7,465,577) or abrogating translation of RNAs encoding one or more of the beta-mannosyltransferases using interfering RNA, antisense RNA, or the like. The scope of the present invention includes methods for producing one or more heterologous polypeptides comprising (i) introducing a polynucleotide encoding the heterologous polypeptide(s) into such a $crz1^{mutant}$, β-mannosyltransferase$^-$ (e.g., bmt1$^-$, bmt2$^-$, bmt3$^-$, and/or bmt4$^-$) host cell and (ii) culturing the host cell under conditions favorable to expression of the heterologous polypeptide(s) in the cell and, optionally, (iii) isolating the heterologous polypeptide(s) from the host cell.

Isolated $cry1^{mutant}$ fungal host cells (e.g., Pichia, e.g., Pichia pastoris) of the present invention also include those that are genetically engineered to eliminate glycoproteins having phosphomannose residues, e.g., by deleting or disrupting one or both of the phosphomannosyl transferase genes PNO1 and MNN4B (See for example, U.S. Pat. Nos. 7,198,921 and 7,259,007), which can include deleting or disrupting one or more of the phosphomannosyltransferases or abrogating translation of RNAs encoding one or more of the phosphomannosyltransferases using interfering RNA, antisense RNA, or the like. In an embodiment of the invention, such fungal host cells produce glycoproteins that have predominantly an N-glycan selected from the group consisting of complex N-glycans, hybrid N-glycans, and high mannose N-glycans wherein complex N-glycans are, in an embodiment of the invention, selected from the group consisting of $Man_3GlcNAc_2$, $GlcNAC_{(1-4)})Man_3GlcNAc_2$, $NANA_{(1-4)}GlcNAc_{(1-4)}Man_3GlcNAc_2$, and $NANA_{(1-4)}Gal_{(1-4)}Man_3GlcNAc_2$; hybrid N-glycans are, in an embodiment of the invention, selected from the group consisting of $Man_5GlcNAc_2$, $GlcNAcMan_5GlcNAc_2$, $GalGlcNAcMan_5GlcNAc_2$, and $NANAGalGlcNAcMan_5GlcNAc_2$; and high mannose N-glycans are, in an embodiment of the invention, selected from the group consisting of $Man_6GlcNAc_2$, $Man_7GlcNAc_2$, $Man_8lcNAc_2$, and $Man_9GlcNAc_2$. The scope of the present invention includes methods for producing one or more heterologous polypeptides comprising (i) introducing a polynucleotide encoding the heterologous polypeptide(s) into such a $cry1^{mutant}$, phosphomannosyl transferase$^-$ (e.g., pno1$^-$ and/or mnn4b$^-$) host cell and (ii) culturing the host cell under conditions favorable to expression of the heterologous polypeptide(s) in the cell and, optionally, (iii) isolating the heterologous polypeptide(s) from the host cell.

Isolated $crz1^{mutant}$ fungal host cells, such as Pichia host cells (e.g., Pichia pastoris) of the present invention include those that are genetically engineered to include a nucleic acid that encodes the Leishmania sp. single-subunit oligosaccharyltransferase STT3A protein, STT3B protein, STT3C protein, STT3D protein, or combinations thereof such as those described in WO2011/06389. The scope of the present invention includes methods for producing one or more heterologous polypeptides comprising (i) introducing a polynucleotide encoding the heterologous polypeptide(s) into such a $crz1^{mutant}$, (Leishmania STT3A$^+$, Leishmania STT3B$^+$, Leishmania STT3C$^+$, and/or Leishmania STT3D$^+$) host cell and (ii) culturing the host cell under conditions favorable to expression of the heterologous polypeptide(s) in the cell and, optionally, (iii) isolating the heterologous polypeptide(s) from the host cell. Isolated cry1$^{mutant}$ fungal host cells (e.g., *Pichia pastoris*) of the present invention also include those that are genetically engineered to eliminate nucleic acids encoding dolichol-P-Man dependent alpha(1-3) mannosyltransferase, e.g., ALG3, such as described in U.S. Patent Publication No. US2005/0170452. The scope of the present invention includes methods for producing one or more heterologous polypeptides comprising (i) introducing a polynucleotide encoding the heterologous polypeptide(s) into such a crz1$^{mutant}$, alga host cell and (ii) culturing the host cell under conditions favorable to expression of the heterologous polypeptide(s) in the cell and, optionally, (iii) isolating the heterologous polypeptide(s) from the host cell.

Isolated crz1$^{mutant}$ fungal host cells of the present invention, such as *Pichia* cells (e.g., *Pichia pastoris*) expressing a polypeptide having an endomannosidase activity (e.g., human (e.g., human liver), rat or mouse endomanosidase) that is targeted to a vesicular compartment within the host cell are part of the present invention. The scope of the present invention includes methods for producing one or more heterologous polypeptides comprising (i) introducing a polynucleotide encoding the heterologous polypeptide(s) into such a Crz1$^{mutant}$, endomannosidase$^+$ host cell and (ii) culturing the host cell under conditions favorable to expression of the heterologous polypeptide(s) in the cell and, optionally, (iii) isolating the heterologous polypeptide(s) from the host cell.

Isolated cry1$^{mutant}$ fungal host cells, such as *Pichia* cells (e.g., *Pichia pastoris*) of the present invention are, in an embodiment of the invention, engineered for producing a recombinant sialylated glycoprotein in the host cell, e.g., wherein the host cell is selected or engineered to produce recombinant glycoproteins comprising a glycoform selected from the group consisting of Gal$_{(1-4)}$GlcNAc$_{(1-4)}$Man$_3$GlcNAc$_2$, e.g., by a method comprising: (a) transforming, into the crz1$^{mutant}$ fungal host cell, one or more polynucleotides encoding a bifunctional UDP-N-acetylglucosamine-2-epimerase/N-acetylmannosamine kinase, an N-acetylneuraminate-9-phosphate synthase, and a CMP-sialic acid synthase; (b) transforming into the host cell a polynucleotide encoding a CMP-sialic acid transporter; and (c) transforming into the host cell a polynucleotide molecule encoding a 2,6-sialyltransferase catalytic domain fused to a cellular targeting signal peptide, e.g., encoded by nucleotides 1-108 of the *S. cerevisiae* Mnn2; wherein, upon passage of a recombinant glycoprotein through the secretory pathway of the host cell, a recombinant sialylated glycoprotein comprising a glycoform selected from the group consisting of NANA$_{(1-4)}$Gal$_{(1-4)}$GlcNAc$_{(1-4)}$Man$_3$GlcNAc$_2$ glycoform is produced. The scope of the present invention includes methods for producing one or more heterologous polypeptides comprising (i) introducing a polynucleotide encoding the heterologous polypeptide(s) into such a czr1$^{mutant}$, bifunctional UDP-N-acetylglucosamine-2-epimerase/N-acetylmannosamine kinase$^+$, N-acetylneuraminate-9-phosphate synthase$^+$, CMP-Sialic acid synthase$^+$, CMP-sialic acid transporter$^+$, 2,6-sialyltransferase$^+$ fungal host cell and (ii) culturing the host cell under conditions favorable to expression of the heterologous polypeptide(s) in the cell and, optionally, (iii) isolating the heterologous polypeptide(s) from the host cell. In addition, isolated czr1$^{mutant}$ fungal host cells of the present invention, such as *Pichia* cells (e.g., *Pichia pastoris*), are, in an embodiment of the invention, engineered for generating galactosylated proteins, e.g., having a terminal galactose residue and essentially lacking fucose and sialic acid residues on the glycoprotein. In one embodiment of the present invention, the isolated czr1$^{mutant}$ fungal host cell comprises an isolated nucleic acid molecule encoding β-galactosyltransferase activity and at least a polynucleotide encoding UDP-galactose transport activity, UDP-galactose C4 epimerase activity, galactokinase activity or galactose-1-phosphate uridyl transferase, e.g., wherein the host cell is genetically engineered to produce N-linked oligosaccharides having terminal GlcNAc residues and comprising a polynucleotide encoding a fusion protein that in the host cell transfers a galactose residue from UDP-galactose onto a terminal GlcNAc residue of an N-linked oligosaccharide branch of an N-glycan of a glycoprotein, wherein the N-linked oligosaccharide branch is selected from the group consisting of GlcNAcβ1,2-Manα1; GlcNAcβ1,4-Manα1,3, GlcNAcβ1,2-Manα1,6, GlcNAcβ1,4-Manα1,6 and GlcNAcβ1,6-Manα1,6, wherein the host cell is diminished or depleted in dolichyl-P-Man:Man$_5$GlcNAc$_2$-PP-dolichyl α-1,3 mannosyltransferase activity, and wherein the host cell produces a glycoprotein having one or more galactose residues. The scope of the present invention includes methods for producing one or more heterologous polypeptides comprising (i) introducing a polynucleotide encoding the heterologous polypeptide(s) into such a host cell and (ii) culturing the host cell under conditions favorable to expression of the heterologous polypeptide(s) in the cell and, optionally, (iii) isolating the heterologous polypeptide(s) from the host cell.

In an embodiment of the invention, an isolated czr1$^{mutant}$ fungal host cell of the present invention, such as *Pichia* cells (e.g., *Pichia pastoris*) lacks functional OCH1 protein, e.g., wherein endogenous OCH1 is mutated. The scope of the present invention includes methods for producing one or more heterologous polypeptides comprising (i) introducing a polynucleotide encoding the heterologous polypeptide(s) into such a czr1$^{mutant}$, och1$^-$ host cell and (ii) culturing the host cell under conditions favorable to expression of the heterologous polypeptide(s) in the cell and, optionally, (iii) isolating the heterologous polypeptide(s) from the host cell.

Isolated crz1$^{mutant}$ fungal host cells of the present invention, such as *Pichia* cells (e.g., *Pichia pastoris*) expressing a galactosyltransferase e.g., an alpha 1,3-galactosyltransferase or a beta 1,4-galactosyltransferase are part of the present invention. The scope of the present invention includes methods for producing one or more heterologous polypeptides comprising (i) introducing a polynucleotide encoding the heterologous polypeptide(s) into such a crz1$^{mutant}$, galactosyltransferase$^+$ host cell and (ii) culturing the host cell under conditions favorable to expression of the heterologous polypeptide(s) in the cell and, optionally, (iii) isolating the heterologous polypeptide(s) from the host cell.

Isolated crz1$^{mutant}$ fungal host cells of the present invention, such as *Pichia* cells (e.g., *Pichia pastoris*) expressing a nucleotide sugar transporter are part of the present invention.

The scope of the present invention includes methods for producing one or more heterologous polypeptides comprising (i) introducing a polynucleotide encoding the heterologous polypeptide(s) into such a crz1$^{mutant}$, nucleotide sugar transporter$^+$ host cell and (ii) culturing the host cell under conditions favorable to expression of the heterologous polypeptide(s) in the cell and, optionally, (iii) isolating the heterologous polypeptide(s) from the host cell.

Isolated crz1$^{mutant}$ fungal host cells of the present invention, such as *Pichia* cells (e.g., *Pichia pastoris*) expressing a sialyltransferase are part of the present invention. The scope of the present invention includes methods for producing one or more heterologous polypeptides comprising (i) introducing a polynucleotide encoding the heterologous polypeptide(s) into such a crz1$^{mutant}$, sialyltransferase$^+$ host cell and (ii) culturing the host cell under conditions favorable to expression of the heterologous polypeptide(s) in the cell and, optionally, (iii) isolating the heterologous polypeptide(s) from the host cell. Isolated crz1$^{mutant}$ fungal host cells of the present invention, such as *Pichia* cells (e.g., *Pichia pastoris*) expressing an acetylglucosaminyl transferase, e.g., GNT1 or GNT2 or GNT4 are part of the present invention. The scope of the present invention includes methods for producing one or more heterologous polypeptides comprising (i) introducing a polynucleotide encoding the heterologous polypeptide(s) into such a crz1$^{mutant}$, acetylglucosaminyl transferase$^+$ host cell and (ii) culturing the host cell under conditions favorable to expression of the heterologous polypeptide(s) in the cell and, optionally, (iii) isolating the heterologous polypeptide(s) from the host cell.

As used herein, the term "essentially free of" as it relates to lack of a particular sugar residue, such as fucose, or galactose or the like, on a glycoprotein, is used to indicate that the glycoprotein composition is substantially devoid of N-glycans which contain such residues.

Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent.

As used herein, a glycoprotein composition "lacks" or "is lacking" a particular sugar residue, such as fucose or galactose, when no detectable amount of such sugar residue is present on the N-glycan structures. For example, in an embodiment of the present invention, glycoprotein compositions produced by host cells of the invention will "lack fucose," because the cells do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

The scope of the present invention encompasses a diploid isolated fungal host cell wherein only one endogenous chromosomal CRZ1 gene has been mutated, disrupted, truncated or partially or fully deleted and the other endogenous chromosomal CRZ1 gene has not been mutated, disrupted, truncated or partially or fully deleted and encodes a functional CRZ1 polypeptide. Homogeneous diploids lacking functional CRZ1 polypeptide, e.g., because both endogenous chromosomal copies of the CRZ1 gene have been mutated, disrupted, truncated or partially or fully deleted are also part of the present invention.

Protein Expression

The scope of the present invention includes methods for producing one or more heterologous polypeptides comprising (i) introducing a polynucleotide encoding the heterologous polypeptide(s) into such a crz1$^{mutant}$ host cell (e.g., as discussed herein) and (ii) culturing the host cell under conditions favorable to expression of the heterologous polypeptide(s) in the cell, for example, for as long as the cells are viable, and, optionally, (iii) isolating the heterologous polypeptide(s) from the host cell. Methods for expressing heterologous polypeptides in fungal host cells is generally known and conventional in the art.

The present invention encompasses any isolated fungal host cell discussed herein suspended in a liquid culture medium. Any lysate of an isolated fungal host cell discussed herein is also within the scope of the present invention.

The culture conditions used for a fungal host cell expression system can be varied depending on the particular conditions at hand. In an embodiment of the invention, fungal host cells can be grown in liquid culture medium in shaken-flasks or in fermentors (e.g., 1 L, 2 L, 5 L, 10 L, 20 L, 30 L, 50 L, 100 L, 200 L, 500 L, 1000 L, 10,000 L volume). Various growth mediums may be used to culture fungal host cells. In an embodiment of the invention, the medium is at a pH of between pH 3 and 7 (e.g., 3, 4, 5, 6 or 7); in an embodiment of the invention, pH is increased with a base such as ammonium hydroxide. In an embodiment of the invention, the temperature is maintained at about 24° C. or 26° C. or 28° C. or 30° C. or 32° C. or 34° C. In an embodiment of the invention, dissolved oxygen in the growth medium is maintained at about 20% or 30%. In an embodiment of the invention, the growth medium contains yeast nitrogen base (e.g., with ammonium sulfate; with or without essential amino acids), peptone and/or yeast extract. Various supplements may be added to an growth medium such as biotin, dextrose, methanol, glycerol, casamino acids, L-arginine-hydrochloride, ammonium ions (e.g., in the form of ammonium phosphates). In an embodiment of the invention, the growth medium is minimal medium containing yeast nitrogen base, water, a carbon source such as dextrose, methanol or glycerol, biotin and histidine. In an embodiment of the invention, the cell culture comprises trace minerals/nutrients such as copper, iodine, manganese, molybdenum, boron, cobalt, zinc, iron, biotin and/or sulfur, e.g., $CuSO_4$, NaI, $MnSO_4$, $Na_2MoO_4$, $H_3BO_3$, $CoCl_2$, $ZnCl_2$, $FeSO_4$, biotin and/or $H_2SO_4$. In an embodiment of the invention, the cell culture comprises an anti-foaming agent (e.g., silicone).

The present invention encompasses methods for making a heterologous polypeptide (e.g., an immunoglobulin chain or an antibody or antigen-binding fragment thereof) comprising introducing, into an isolated fungal crz1$^{mutant}$ host cell (e.g., *Pichia*, such as *Pichia pastoris*) a heterologous polynucleotide encoding said polypeptide, e.g., that is operably linked to a promoter, e.g., a methanol-inducible promoter and culturing the host cells, (i) in a batch phase (e.g., a glycerol batch phase) wherein the cells are grown with a non-fermentable carbon source, such as glycerol, e.g., until the non-fermentable carbon source is exhausted;

(ii) in a batch-fed phase (e.g., a glycerol batch-fed phase) wherein additional non-fermentable carbon source (e.g., glycerol) is fed, e.g., at a growth limiting rate; and (iii) in a methanol fed-batch phase wherein the cells are grown in the presence of methanol and, optionally, additional glycerol.

In an embodiment of the invention, in the methanol fed-batch phase, methanol concentration is set to about 2 grams methanol/liter to about 5 grams methanol/liter (e.g., 2, 2.5, 3, 3.5, 4, 4.5 or 5).

In an embodiment of the invention, prior to the batch phase, an initial seed culture is grown to a high density (e.g., $OD_{600}$ of about 2 or higher) and the cells grown in the seed culture are used to inoculate the initial batch phase culture medium.

In an embodiment of the invention, after the batch-fed phase and before the methanol fed-batch phase, the host cells are grown in a transitional phase wherein cells are grown in the presence of about 2 ml methanol per liter of culture. For example, the cells can be grown in the transitional phase until the methanol concentration reaches about zero.

Heterologous polypeptides that are isolated from a fungal host cell are, in an embodiment of the invention, purified. If the heterologous polypeptide is secreted from the fungal host cell into the liquid growth medium, the polypeptide can be purified by a process including removal of the fungal host cells from the growth medium. Removal of the cells from the medium may be performed using centrifugation, discarding the cells and retention of the liquid medium supernatant. If the heterologous polypeptide is not secreted, the liquid medium can be discarded after separation from the fungal host cells which are retained. Thereafter, the fungal host cells may be lysed to produce a crude cell lysate from which the heterologous polypeptide may be further purified.

Heterologous polypeptide purification is, in an embodiment of the invention, performed by chromatography, e.g., column chromatography. Chromatographic purification can include the use of ion exchange, e.g., anion exchange and/or cation exchange, protein-A chromatography, size exclusion chromatography and/or hydrophobic interaction chromatography. Purification can also include viral inactivation of the composition comprising the polypeptide, precipitation and/or lyophilization.

EXAMPLES

This section is intended to further describe the present invention and should not be construed to further limit the invention. Any composition or method set forth herein constitutes part of the present invention.

Example 1: Identification of CRZ1 Mutations

Experimental Methods

UV mutagenesis, fed-batch fermentations, IgG purifications, N-glycan characterizations, as well as all other analytical assays, were performed as previously described (Barnard et al. 2010; Jiang et al. 2011; Potgieter et al. 2009; Winston F 2008). Except otherwise specified, all 1 L Bioreactor fermentation runs were scheduled to end after 100-120 hours of MeOH induction. However, a fermentation run was terminated prematurely if excess cell lysis was observed. Cell lysis was determined either by microscopic examination, or by measuring the amount of nuclear DNA released into the supernatant (Barnard, 2010). Excess cell lysis was defined by either greater than 90% cells lysed by microscopic examination, or greater than 30 microgram/ml DNA concentration in the supernatant determined by Picogreen assay.

Result and Discussion

Temperature-Resistant Mutants Displayed Substantially Enhanced Fermentation Robustness.

To identify Pichia host strains with increased fermentation robustness, we UV-mutagenized temperature-sensitive glyco-engineered strains (YGLY12905, YGLY22835, and YGLY27890), and selected for temperature-resistant mutants, with the rationale that certain $2^{nd}$-site mutations suppressing the temperature-sensitive defect might also compensate for the cell robustness deficiency. After confirming their temperature-resistant phenotypes, these mutants were fermented using standard MeOH fed-batch runs in 1 L DasGip Bioreactors. After an extensive fermentation screening campaign, we identified 9 mutants displaying much enhanced cell robustness during the fermentation process. As shown in FIG. 1, the fermentation process for the non-mutagenized control strain had to be terminated, due to excessive cell lysis, at approximately 48 hours of induction at 32° C. In contrast, the mutants all displayed significantly improved fermentation robustness. YGLY29010, YGLY29030, YGLY29031, and YGLY29012 were able to ferment approximately 90 hours; YGLY28997, YGLY28998, YGLY17159, YGLY28999, and YGLY29042 all lasted for more than 100 hours induction at 32° C.

Protein Productivity and N-glycan Quality Assessments of the Temperature-Resistant Mutants.

Figure 2A:
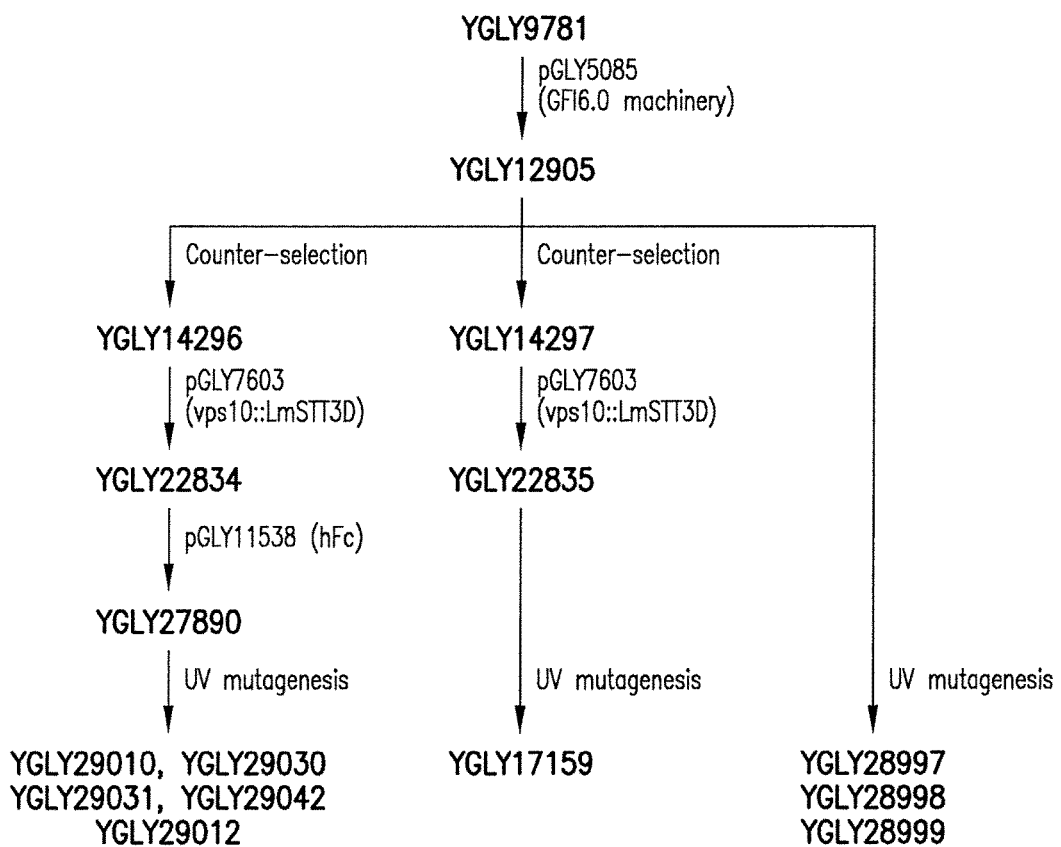
FIG. 2(*a-c*): Lineages of mutagenized *Pichia pastoris* strains.
Figure 2B:
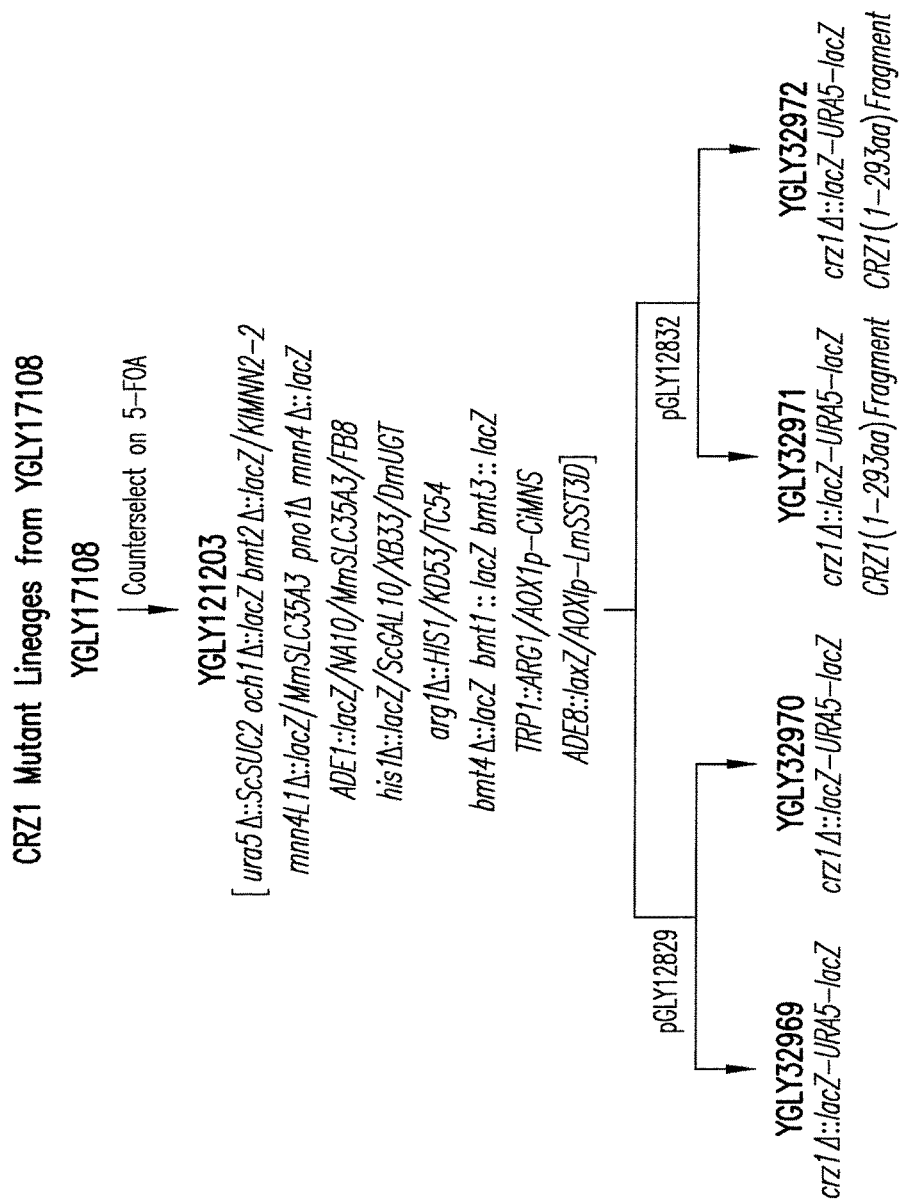
Figure 2C:
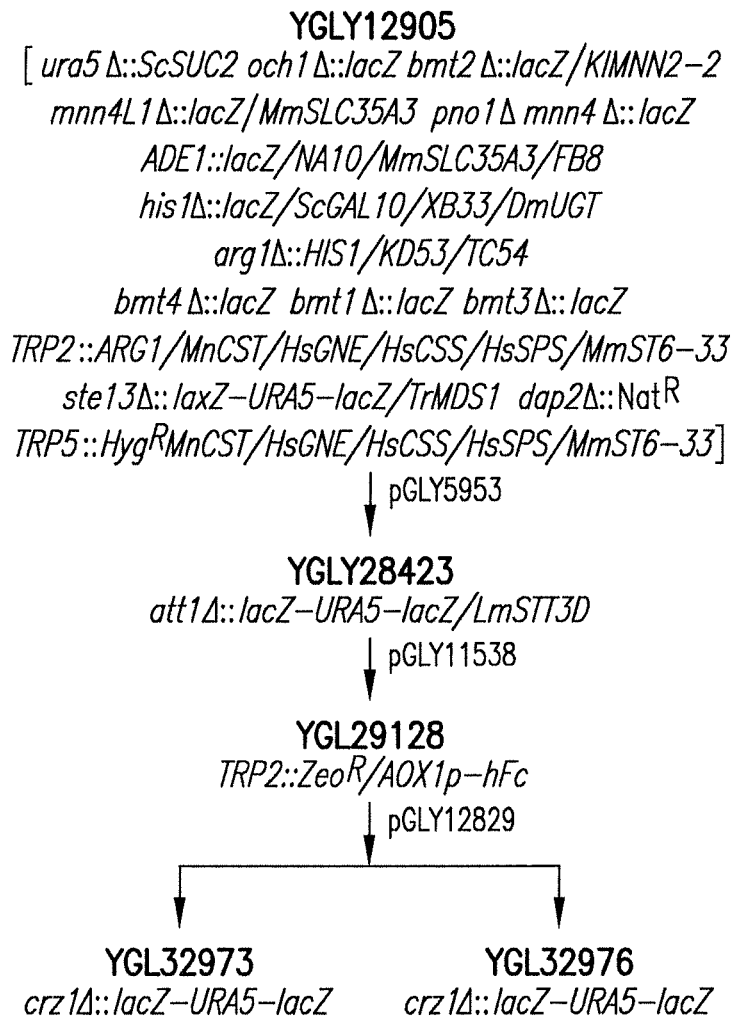
Figure 3:
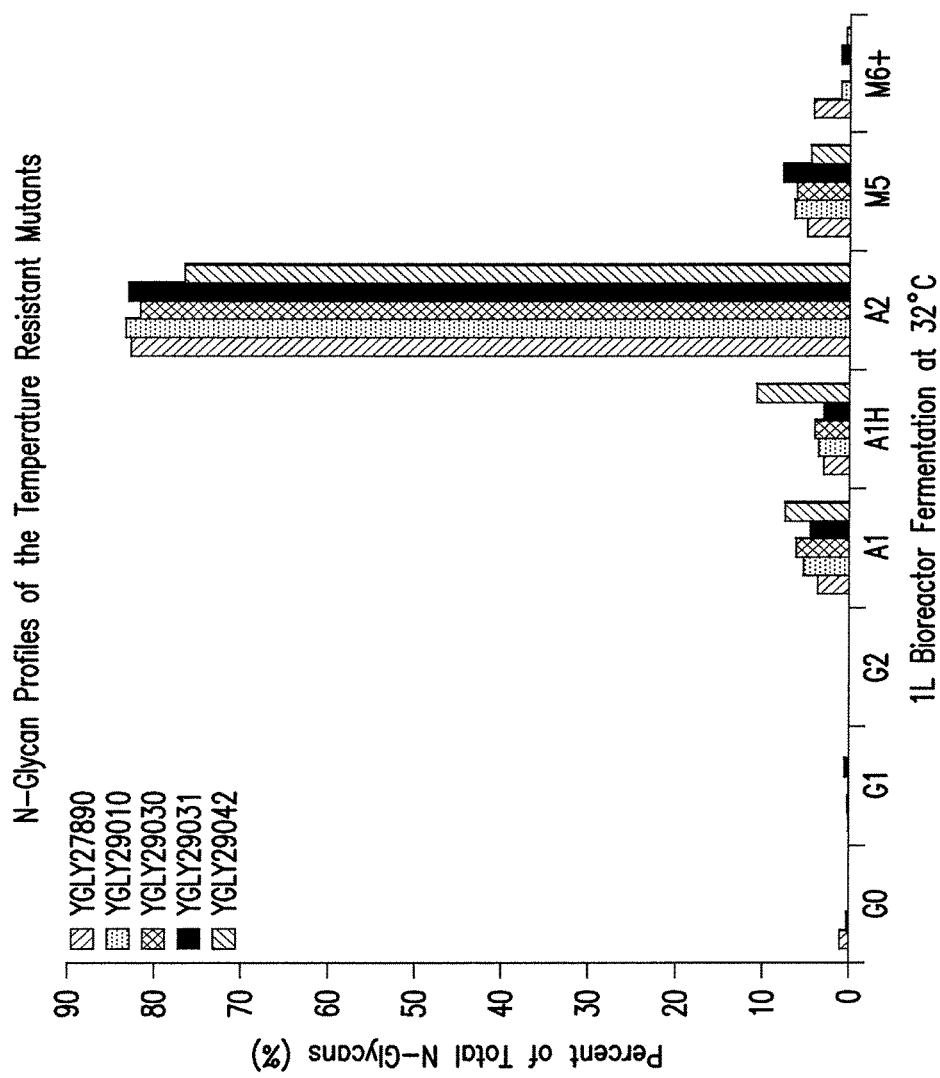
FIG. 3: N-Glycan profiles of the temperature resistant mutants. G0=N-glycan terminated by GlcNac; G1=Singly galactose terminated N-glycan; G2=Doubly galactose terminated N-glycan; A1=Singly sialic acid terminated N-glycan; A1H=A1 hybrid, singly sialic acid terminated N-glycan with a hybrid structure; A2=Doubly sialic acid terminated N-glycan; M5=Man$_5$; M6+=Man$_{6+}$.

Five of the temperature-resistant mutants (YGLY29010, YGLY29030, YGLY29031, YGLY29042, and YGLY29012) were derived from YGLY27890 (FIG. 2), which expresses a human Fc fragment. To evaluate what impacts these temperature-resistant mutations had on Fc productivity and N-glycan quality, we purified the Fc fragments from the 32° C. 1 L bioreactors, quantified the broth titer (FIG. 1), and analyzed the N-glycan profiles (FIG. 3) of four temperature-resistant mutants, as well as their un-mutagenized parent strain YGLY27890. Compared with the parental control, four mutants (YGLY29010, YGLY29030, YGLY29031, and YGLY29042) displayed substantial increases in product titers: in fact, YGLY29042 and YGLY29010 actually secreted approximately 4-5 fold more Fc product. In contrast, the product titer from YGLY29012 was only approximately 50% of the control strain's titer. For N-glycans derived from the Fc product, we did not observe any significant alterations in the N-glycan profiles (FIG. 3). Just like the control strain YGLY27890 (83% A2 and 4% A1), all five mutants were able to effectively modify their Fc N-glycans with high levels of terminal sialic acids, with A2 levels ranging from 77 to 84%, and A1 levels from 4 to 7%. Collectively, these results demonstrated that the UV-induced mutations acquired by YGLY29010, YGLY29030, YGLY29031, and YGLY29042 did not negatively affect their capabilities for producing heterologously expressed human Fc fragment, nor did the mutations resulted in noticeable deteriorations in N-glycan quality.

Genome Sequencing to Identify the Causative Mutation(s) Responsible for the Enhanced Thermal-tolerance and Fermentation Robustness.

Figure 5:
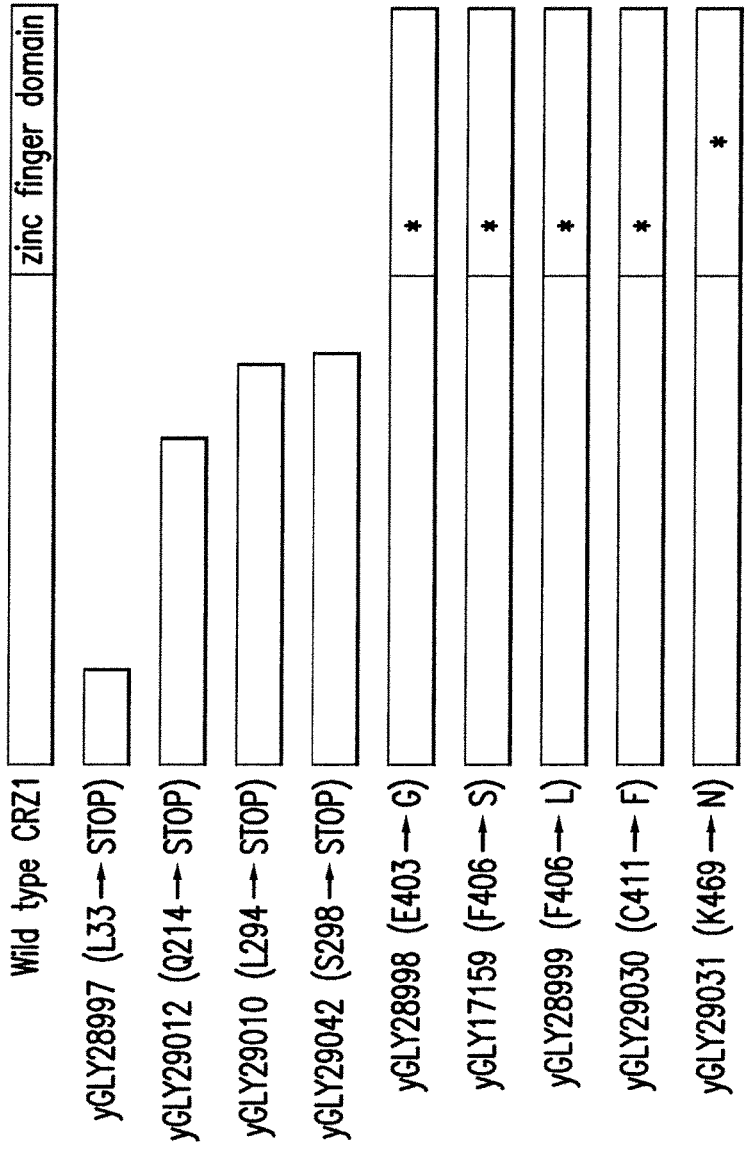
FIG. 5: Mutated protein Pp02g02120 was homologous to *Saccharomyces cerevisiae* CRZ1 zinc finger transcription factor involved in stress responses. The various isolated mutant PpCRZ1 alleles are shown. The "*" shows the location of the indicated mutation.

In order to better understand the molecular mechanisms involved in maintaining cell robustness during fermentation, we sequenced the genomes of these 9 temperature-resistant mutants, as well as two un-mutagenized empty host strains YGLY22812 and YGLY22835. After genome-wide comparisons between the mutants and the un-mutagenized strains, we identified between 1 to 7 non-synonymous mutations (indicated by a "+" FIG. 4) in each of these 9 mutants. Three mutants, YGLY29010, YGLY29031, and YGLY29042, contained a single mutation within a gene, Pp02g02120, which showed a high-level of sequence homology to the CRZ1 gene of Saccharomyces cerevisiae. Remarkably, distinct mutations in the same PpCRZ1 gene were also detected in YGLY28997, YGLY28998, YGLY17159, YGLY28999, YGLY29030, and YGLY29012. ScCRZ1 is a calcineurin-responsive zinc finger transcription factor involved in stress responses. The zinc finger domains are very well conserved between PpCRZ1 and ScCRZ1, and are both located at the c-terminal end (see sequence alignment above). As illustrated in FIG. 5, the four non-sense, stop-codon mutations found from the temperature-resistant mutants were located upstream of the zinc-finger, thus all giving rise to truncated PpCRZ1 fragments without the zinc-finger domain. For the remaining 5 mutants, they contain mis-sense, amino-acid substitution mutations, all of which located within the zinc-finger domain, with 4 of them clustered within 25 nucleotides. The findings that 9 independently isolated temperature-resistant mutants contained different non-sense or mis-sense mutation within the PpCRZ1 gene strongly suggested that these CRZ1 mutations were causative for the temperature-resistant and increased fermentation robustness phenotypes. Furthermore, 2 of the mutants (yGLY17159 and yGLY28998) also harbored additional mutations in PpATT1, which is a gene previously shown to play critical roles in temperature-tolerance and cell robustness as well. The fact that both yGLY17159 and yGLY28998 were among the most robust mutants isolated suggested the combination of ATT1 and CRZ1 mutations might have additive or synergistic effects for increasing thermal-tolerance and fermentation robustness in glyco-engineered *Pichia* strains.

PpCRZ1 Sequences.

1. *Pichia pastoris* CRZ1 wild-type open reading frame
(SEQ ID NO: 2)

```
ATGGCAGACCAACGGCTTGAGGATGAGTTTGATATCTCCAGATACTTATCTATTTCTCCTATCGAGTCAG
CTTCAATCGAAGAATCAATCAACGGTTTAATGAGTAGTTGGATTCCTCCGGCTAAGGGTGAGATTAGAGA
TTCACTTCCTCCAAACGCTTCTTTTGAAGCTACAGACAGTTTTTCAACCAGTTCATACCAGGAAATTATA
CCAGCACAGGTGAAAATAAAACTGGAGTTTGATAATGACCAGCAGCCTGTTTTCTATCTAGAATCGCAAC
CAGTTTATGATAAGCATTTAACCGTCAATGATCAGGAAACCAGAAGCGCCCAAGACTTCAACCAATACTT
GAATGCTGATGCCGTATCGAGGACCAACTCCATCTCCAACTTATCGGAGCTGTCAACTCATTCCCATATT
ACCCCTCCAACGCTACTTCATGATCAAGCCTCATTGTCTCCTGCTCTCTTATCTATGAACAGTGATGAAA
GAAACGAACTCAATCTGGAAACACTACAGCTAGATCAAACGTCACAGCCTTACGTGAATCAGATAAAAAC
GGAGGCAGCTTACGAAGAGCTTTCAGAGTTACACCACAGATTAGAAAGACTCACTGAGACAAATTTAATT
CATCTAGACCAGCTTCTACTCGAACTACTAGAGCAACAAAATCAGACTCCTCATACTCTCAGTCCTCCTA
TACAACTTCAGACTCCCATAATCAAAGTCTTGCAAGCCCCAAATGATATAGCAGCAAATACCCCGTCTCT
TTTTTCTCAATCTAACCATTCATCTCCATATAACACACCCAAACATTCCAGGTCAAACTCGTTGAGTTCA
AATGACAGACAACATGATATTCCACAAATATCCTCAGTTTTAGACACGTCTTCGTTTTTGGTACCTGGAG
ATCAGTTTCAAGCAATGAGAGAAGGTAGACAGAGGAGGAAATCCGAGTCCAACTCTAGAAACTCGAAAGA
ACGTTCTAAATCTAGGGAACCGCCAAAGTCCAGGTCTAGATCTAGAGACAGTGCAACAGATCATCATATG
GAAGTTATGAGCAGAGAAAAGACTCTTGAGTTGGCAGCTTCTCAGCCAAGCTCCAAGACGCCGCAAAAGA
ACCCTTCCATCTATGCTTGCTCGCTCTGCTCCAAGAGATTCACAAGACCATATAATTTGAAGTCTCACCT
TCGCACGCACGCTGATGAAAGGCCTTTCCAGTGTTCAATATGCGGGAAGGCATTTGCTCGTTCTCACGAC
AGAAAGCGTCATGAGGATCTGCATAGTGGTGAACGAAAGTATTGCTGCAAAGGTGTTTTGTCTGACGGAG
TAACTACATGGGGCTGTGAAAAAAGATTTGCCCGAACAGATGCGCTGGGTAGACATTTCAAAACTGAATG
TGGTAAACTGTGTATCAAGCCGCTGATGGATGAACTAAAGAGGGAGGAAGCTTACAGGAGGAATGAACCA
GTAACAGAAATGAATGACGAGCTTTACTCCCAATCTGTCCAAGATATATTTAGCTCTCAGCGGCTTGGTC
AGAACATAGATGACtga
```

2. *Pichia pastoris* mutant CRZ1 isolated from yGLY28997 (encoding the mutation: L33→STOP, mutated nucleotide is in bold font)
(SEQ ID NO: 2 comprising t98a mutation)

```
ATGGCAGACCAACGGCTTGAGGATGAGTTTGATATCTCCAGATACTTATCTATTTCTCCTATCGAGTCAG
CTTCAATCGAAGAATCAATCAACGGTTAAATGAGTAGTTGGATTCCTCCGGCTAAGGGTGAGATTAGAGA
TTCACTTCCTCCAAACGCTTCTTTTGAAGCTACAGACAGTTTTTCAACCAGTTCATACCAGGAAATTATA
CCAGCACAGGTGAAAATAAAACTGGAGTTTGATAATGACCAGCAGCCTGTTTTCTATCTAGAATCGCAAC
CAGTTTATGATAAGCATTTAACCGTCAATGATCAGGAAACCAGAAGCGCCCAAGACTTCAACCAATACTT
GAATGCTGATGCCGTATCGAGGACCAACTCCATCTCCAACTTATCGGAGCTGTCAACTCATTCCCATATT
ACCCCTCCAACGCTACTTCATGATCAAGCCTCATTGTCTCCTGCTCTCTTATCTATGAACAGTGATGAAA
GAAACGAACTCAATCTGGAAACACTACAGCTAGATCAAACGTCACAGCCTTACGTGAATCAGATAAAAAC
GGAGGCAGCTTACGAAGAGCTTTCAGAGTTACACCACAGATTAGAAAGACTCACTGAGACAAATTTAATT
```

-continued

```
CATCAAGACCAGCTTCAACTCGAACAACAAGAGCAACAAAATCAGACTCCTCATACTCTCAGTCCTCCTA
TACAACTTCAGACTCCCATAATCAAAGTCTTGCAAGCCCCAAATGATATAGCAGCAAATACCCCGTCTCT
TTTTTCTCAATCTAACCATTCATCTCCATATAACACACCCAAACATTCCAGGTCAAACTCGTTGAGTTCA
AATGACAGACAACATGATATTCCACAAATATCCTCAGTTTTAGACACGTCTTCGTTTTTGGTACCTGGAG
ATCAGTTTCAAGCAATGAGAGAAGGTAGACAGAGGAGGAAATCCGAGTCCAACTCTAGAAACTCGAAAGA
ACGTTCTAAATCTAGGGAACCGCCAAAGTCCAGGTCTAGATCTAGAGACAGTGCAACAGATCATCATATG
GAAGTTATGAGCAGAGAAAAGACTCTTGAGTTGGCAGCTTCTCAGCCAAGCTCCAAGACGCCGCAAAAGA
ACCCTTCCATCTATGCTTGCTCGCTCTGCTCCAAGAGATTCACAAGACCATATAATTTGAAGTCTCACCT
TCGCACGCACGCTGATGAAAGGCCTTTCCAGTGTTCAATATGCGGGAAGGCATTTGCTCGTTCTCACGAC
AGAAAGCGTCATGAGGATCTGCATAGTGGTGAACGAAAGTATTGCTGCAAAGGTGTTTTGTCTGACGGAG
TAACTACATGGGCTGTGAAAAAGATTTGCCCGAACAGATGCGCTGGGTAGACATTTCAAAACTGAATG
TGGTAAACTGTGTATCAAGCCGCTGATGGATGAACTAAAGAGGGAGGAAGCTTACAGGAGGAATGAACCA
GTAACAGAAATGAATGACGAGCTTTACTCCCAATCTGTCCAAGATATATTTAGCTCTCAGCGGCTTGGTC
AGAACATAGATGACtga
```

3. *Pichia pastoris* mutant CRZ1 isolated from yGLY29012 (encoding the mutation: Q214→STOP, mutated nucleotide is in bold font)

(SEQ ID NO: 2 comprising c640t mutation)

```
ATGGCAGACCAACGGCTTGAGGATGAGTTTGATATCTCCAGATACTTATCTATTTCTCCTATCGAGTCAG
CTTCAATCGAAGAATCAATCAACGGTTTAATGAGTAGTTGGATTCCTCCGGCTAAGGGTGAGATTAGAGA
TTCACTTCCTCCAAACGCTTCTTTTGAAGCTACAGACAGTTTTTCAACCAGTTCATACCAGGAAATTATA
CCAGCACAGGTGAAAATAAAACTGGAGTTTGATAATGACCAGCAGCCTGTTTTCTATCAAGAATCGCAAC
CAGTTTATGATAAGCATTTAACCGTCAATGATCAGGAAACCAGAAGCGCCCAAGACTTCAACCAATACTT
GAATGCTGATGCCGTATCGAGGACCAACTCCATCTCCAACTTATCGGAGCTGTCAACTCATTCCCATATT
ACCCCTCCAACGCTACTTCATGATCAAGCCTCATTGTCTCCTGCTCTCTTATCTATGAACAGTGATGAAA
GAAACGAACTCAATCTGGAAACACTACAGCTAGATCAAACGTCACAGCCTTACGTGAATCAGATAAAAAC
GGAGGCAGCTTACGAAGAGCTTTCAGAGTTACACCACAGATTAGAAAGACTCACTGAGACAAATTTAATT
CATCAAGACTAGCTTCAACTCGAACAACAAGAGCAACAAAATCAGACTCCTCATACTCTCAGTCCTCCTA
TACAACTTCAGACTCCCATAATCAAAGTCTTGCAAGCCCCAAATGATATAGCAGCAAATACCCCGTCTCT
TTTTTCTCAATCTAACCATTCATCTCCATATAACACACCCAAACATTCCAGGTCAAACTCGTTGAGTTCA
AATGACAGACAACATGATATTCCACAAATATCCTCAGTTTTAGACACGTCTTCGTTTTTGGTACCTGGAG
ATCAGTTTCAAGCAATGAGAGAAGGTAGACAGAGGAGGAAATCCGAGTCCAACTCTAGAAACTCGAAAGA
ACGTTCTAAATCTAGGGAACCGCCAAAGTCCAGGTCTAGATCTAGAGACAGTGCAACAGATCATCATATG
GAAGTTATGAGCAGAGAAAAGACTCTTGAGTTGGCAGCTTCTCAGCCAAGCTCCAAGACGCCGCAAAAGA
ACCCTTCCATCTATGCTTGCTCGCTCTGCTCCAAGAGATTCACAAGACCATATAATTTGAAGTCTCACCT
TCGCACGCACGCTGATGAAAGGCCTTTCCAGTGTTCAATATGCGGGAAGGCATTTGCTCGTTCTCACGAC
AGAAAGCGTCATGAGGATCTGCATAGTGGTGAACGAAAGTATTGCTGCAAAGGTGTTTTGTCTGACGGAG
TAACTACATGGGCTGTGAAAAAGATTTGCCCGAACAGATGCGCTGGGTAGACATTTCAAAACTGAATG
TGGTAAACTGTGTATCAAGCCGCTGATGGATGAACTAAAGAGGGAGGAAGCTTACAGGAGGAATGAACCA
GTAACAGAAATGAATGACGAGCTTTACTCCCAATCTGTCCAAGATATATTTAGCTCTCAGCGGCTTGGTC
AGAACATAGATGACtga
```

-continued

4. *Pichia pastoris* mutant CRZ1 isolated from yGLY29010 (encoding the mutation: L294→STOP, mutated nucleotide is in bold font)
(SEQ ID NO: 2 comprising t881g mutation)

ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCTAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTGAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTTTCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGCTGTGAAAAAGATTTGCCCGAACAGATGCGCTGGGTAGACATTTCAAAACTGAATG

TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga

5. *Pichia pastoris* mutant CRZ1 isolated from yGLY29042 (encoding the mutation: S298→STOP, mutated nucleotide is in bold font)
(SEQ ID NO: 2 comprising c893a mutation)

ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATTATGACCAGCAGCCTGTTTTCTATCTAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTTAGACACGTCTTAGTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

-continued

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTTTCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGCTGTGAAAAAGATTTGCCCGAACAGATGCGCTGGGTAGACATTTCAAAACTGAATG

TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga

6. *Pichia pastoris* mutant CRZ1 isolated from yGLY28998 (encoding
the mutation: E403→G, mutated nucleotide is in bold font)
(SEQ ID NO: 2 comprising a1208g mutation)
ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCAAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTTAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGGAAGGCCTTTCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGCTGTGAAAAAGATTTGCCCGAACAGATGCGCTGGGTAGACATTTCAAAACTGAATG

TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga

7. *Pichia pastoris* mutant CRZ1 isolated from yGLY17159 (encoding
the mutation: F406→S, mutated nucleotide is in bold font)
(SEQ ID NO: 2 comprising t1217c mutation)
ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCAAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

```
ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTTAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTTCCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGGCTGTGAAAAAAGATTTGCCCGAACAGATGCGCTGGGTAGACATTTCAAAACTGAATG

TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga
```

8. *Pichia pastoris* mutant CRZ1 isolated from yGLY28999 (encoding
the mutation: F406→L, mutated nucleotide is in bold font)
                            (SEQ ID NO: 2 comprising t1216c mutation)

```
ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCAAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTTAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTCTCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGGCTGTGAAAAAAGATTTGCCCGAACAGATGCGCTGGGTAGACATTTCAAAACTGAATG
```

```
TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga
```

9. *Pichia pastoris* mutant CRZ1 isolated from yGLY29030 (encoding the mutation: C411→F, mutated nucleotide is in bold font)
(SEQ ID NO: 2 comprising g1232t mutation)

```
ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCTAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA

AATGACAGACAACATGATATTCCACAAATATCCTCAGTTTTAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTTTCCAGTGTTCAATATTCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGGCTGTGAAAAAAGATTTGCCCGAACAGATGCGCTGGGTAGACATTTCAAAACTGAATG

TGGTAAACTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga
```

10. *Pichia pastoris* mutant CRZ1 isolated from yGLY29031 (encoding the mutation: K469→N, mutated nucleotide is in bold font)
(SEQ ID NO: 2 comprising a1407c mutation)

```
ATGGCAGACCAACGGCTTGAGGATGAGTTTGATATCTCCAGATACTTATCTATTTCTCCTATCGAGTCAG

CTTCAATCGAAGAATCAATCAACGGTTTAATGAGTAGTTGGATTCCTCCGGCTAAGGGTGAGATTAGAGA

TTCACTTCCTCCAAACGCTTCTTTTGAAGCTACAGACAGTTTTTCAACCAGTTCATACCAGGAAATTATA

CCAGCACAGGTGAAAATAAAACTGGAGTTTGATAATGACCAGCAGCCTGTTTTCTATCAAGAATCGCAAC

CAGTTTATGATAAGCATTTAACCGTCAATGATCAGGAAACCAGAAGCGCCCAAGACTTCAACCAATACTT

GAATGCTGATGCCGTATCGAGGACCAACTCCATCTCCAACTTATCGGAGCTGTCAACTCATTCCCATATT

ACCCCTCCAACGCTACTTCATGATCAAGCCTCATTGTCTCCTGCTCTCTTATCTATGAACAGTGATGAAA

GAAACGAACTCAATCTGGAAACACTACAGCTAGATCAAACGTCACAGCCTTACGTGAATCAGATAAAAAC

GGAGGCAGCTTACGAAGAGCTTTCAGAGTTACACCACAGATTAGAAAGACTCACTGAGACAAATTTAATT

CATCAAGACCAGCTTCAACTCGAACAACAAGAGCAACAAAATCAGACTCCTCATACTCTCAGTCCTCCTA

TACAACTTCAGACTCCCATAATCAAAGTCTTGCAAGCCCCAAATGATATAGCAGCAAATACCCCGTCTCT

TTTTTCTCAATCTAACCATTCATCTCCATATAACACACCCAAACATTCCAGGTCAAACTCGTTGAGTTCA
```

-continued

```
AATGACAGACAACATGATATTCCACAAATATCCTCAGTTTTAGACACGTCTTCGTTTTTGGTACCTGGAG

ATCAGTTTCAAGCAATGAGAGAAGGTAGACAGAGGAGGAAATCCGAGTCCAACTCTAGAAACTCGAAAGA

ACGTTCTAAATCTAGGGAACCGCCAAAGTCCAGGTCTAGATCTAGAGACAGTGCAACAGATCATCATATG

GAAGTTATGAGCAGAGAAAAGACTCTTGAGTTGGCAGCTTCTCAGCCAAGCTCCAAGACGCCGCAAAAGA

ACCCTTCCATCTATGCTTGCTCGCTCTGCTCCAAGAGATTCACAAGACCATATAATTTGAAGTCTCACCT

TCGCACGCACGCTGATGAAAGGCCTTTCCAGTGTTCAATATGCGGGAAGGCATTTGCTCGTTCTCACGAC

AGAAAGCGTCATGAGGATCTGCATAGTGGTGAACGAAAGTATTGCTGCAAAGGTGTTTTGTCTGACGGAG

TAACTACATGGGGCTGTGAAAAAAGATTTGCCCGAACAGATGCGCTGGGTAGACATTTCAAAACTGAATG

TGGTAACCTGTGTATCAAGCCGCTGATGGATGAACTAAAGAGGGAGGAAGCTTACAGGAGGAATGAACCA

GTAACAGAAATGAATGACGAGCTTTACTCCCAATCTGTCCAAGATATATTTAGCTCTCAGCGGCTTGGTC

AGAACATAGATGACtga
```

Example 2: Confirmation of Phenotype by Directed Strain Engineering

Figure 8:
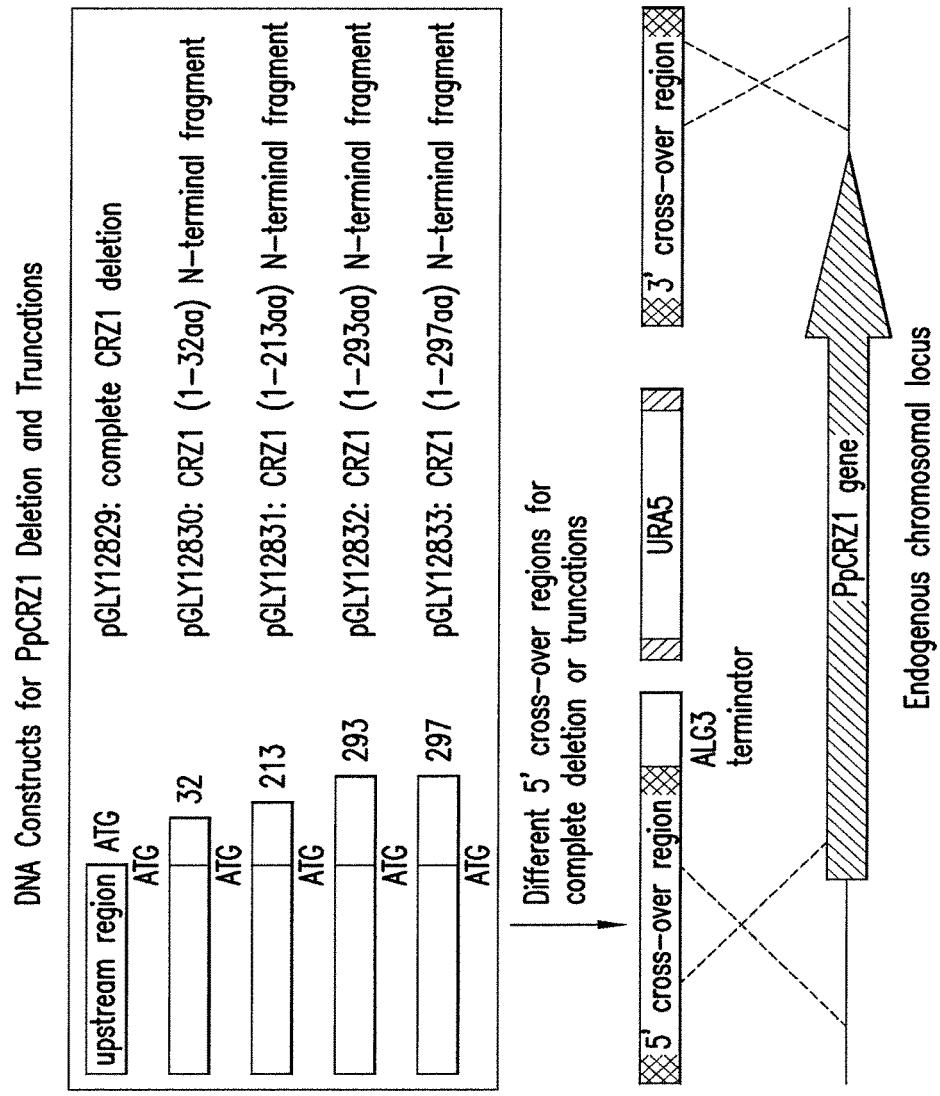
FIG. 8: DNA Constructs constructed for *Pichia pastoris* CRZ1 deletion and truncations.

As discussed herein, independent mutations in the same CRZ1 gene in each of the mutants strongly indicated that inactivation of this transcription factor is responsible for the observed temperature-resistance and fermentation robustness phenotypes. To confirm this conclusion, the CRZ1 ORF was either completely deleted, or the endogenous CRZ1 gene was replaced with the truncated versions shown in FIG. 8, in YGLY21203, which is a non-mutagenized ura5 auxtroph Pichia strain derived from YGLY17108 by 5-FOA counter-selection.

Figure 6:
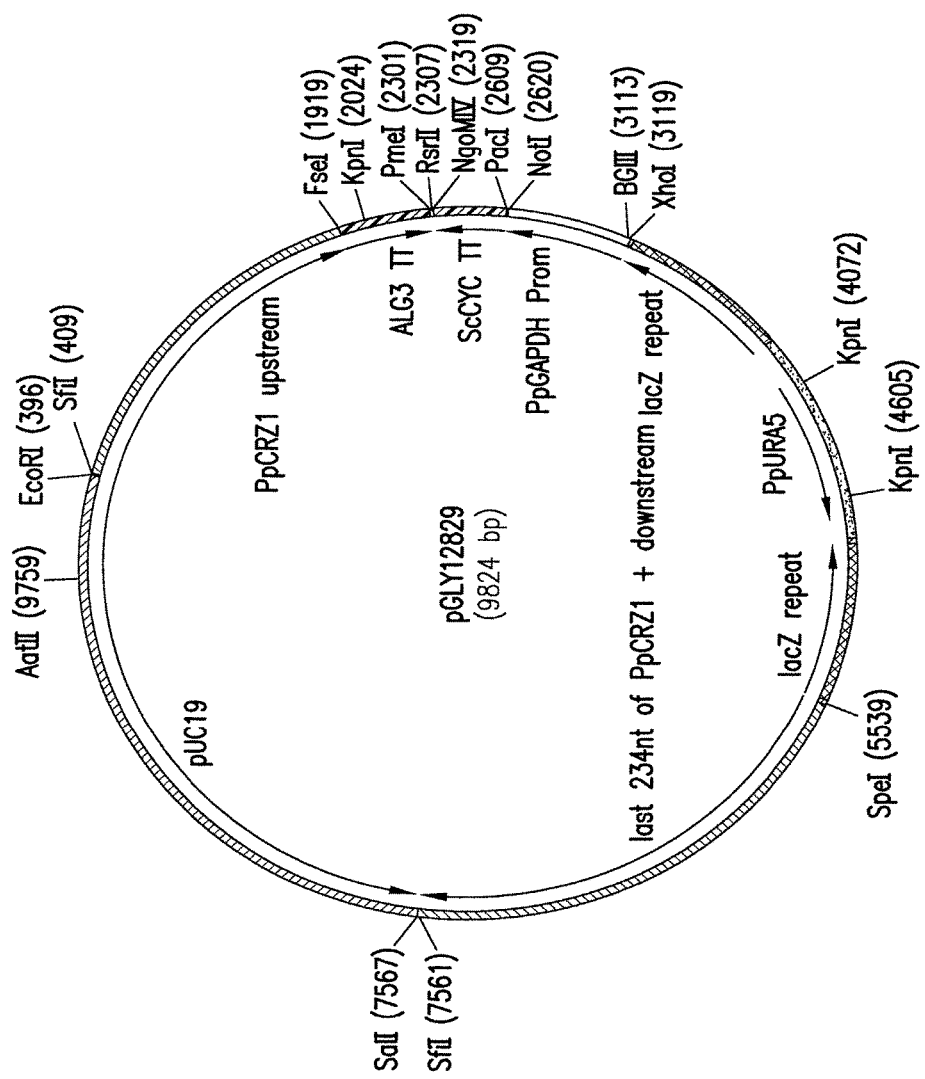
FIG. 6: Plasmid pGLY12829.
Figure 7:
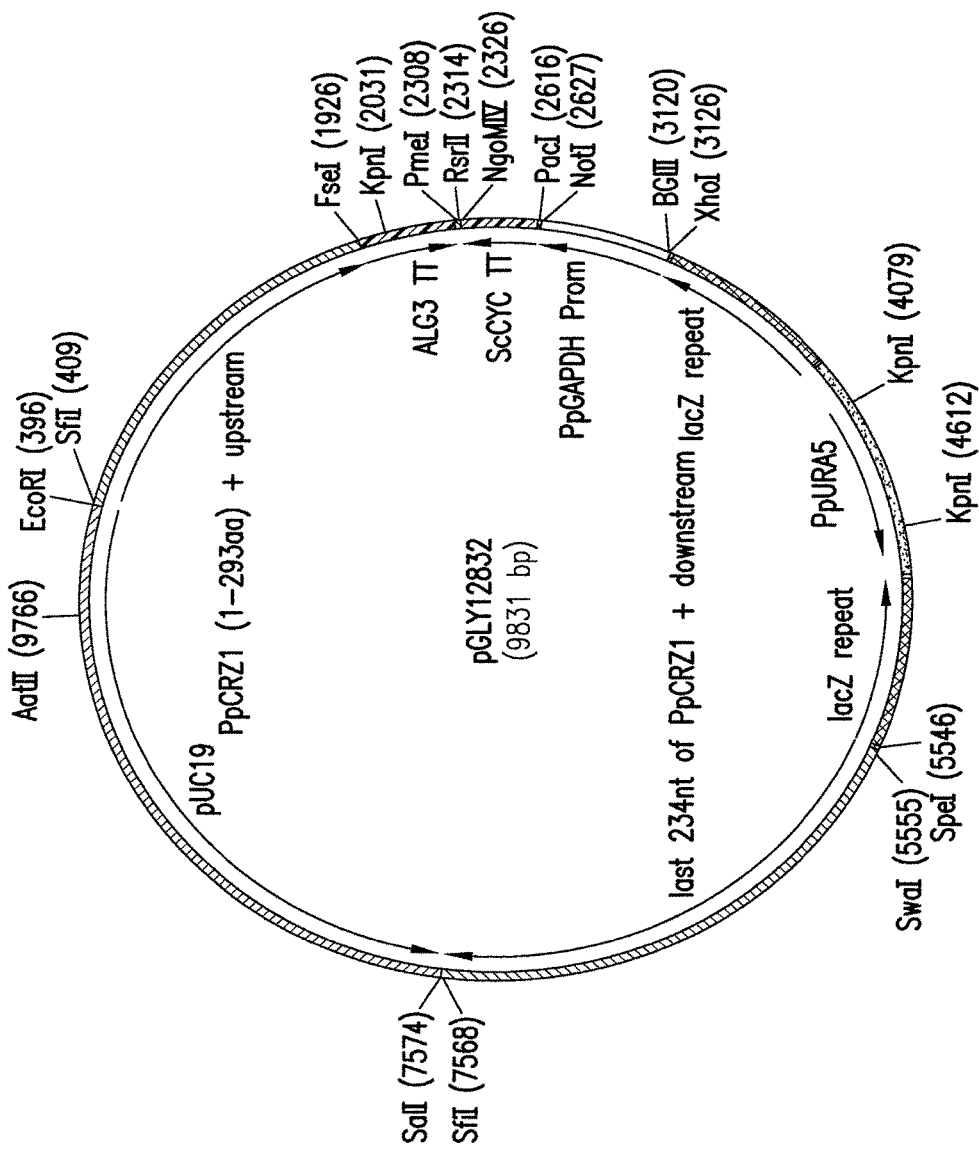
FIG. 7: Plasmid pGLY12832.

Plasmid pGLY12829 (FIG. 6) was constructed by cloning a 1.5 kb genomic DNA fragment immediately upstream of the CRZ1 ORF in front of the ALG3 terminator, followed by the lacZ-URA5-lacZ URAblaster, and then connected to a 2 kb genomic DNA fragment containing the last 234 by of the CRZ1 ORF plus 1.7 kb of the downstream region. After SfiI digestion, this CRZ1-upstream-URAblaster-CRZ1-downstream DNA fragment was transformed into a non-mutagenized host strain (e.g., YGLY17108). By homologous recombination at both the CRZ1 upstream and downstream regions, this URAblaster-cassette replaced the endogenous CRZ1 gene, deleting 85% of CRZ1's coding region, thus generating a complete CRZ1 knock-out mutant. To confirm the correct replacement of the CRZ1 ORF, genomic DNA polymerase chain reaction (PCR) assays were conducted using the following oligonucleotides as PCR primers: GTATGCGATATAGTGTGGA (SEQ ID NO: 4, 1545 by upstream of CRZ1 start) and TGGGGAGAAGGTAC-CGAAG (SEQ ID NO: 5, within the ALG3 terminator) to confirm the 5' junction of the gene-replacement; CAC-TACGCGTACTGTGAGCC (SEQ ID NO: 6, within the lacZ) and AGGATATCAAACCCGACCAG (SEQ ID NO: 7, 2045 by downstream of the CRZ1 stop codon) to confirm the 3' junction of the gene-replacement; plus "GACACAT-GCGAAATGTCCTG" (SEQ ID NO:8, 120 by downstream of the CRZ1 stop codon) and "TTGAGTTGGCAGCT-TCTCAG" (SEQ ID NO: 9, within the CRZ1 ORF, 1075 by after the start) to confirm the absence of the wild-type CRZ1 ORF. Plasmid pGLY12832 (FIG. 7) was constructed by cloning a 1.5 kb DNA fragment (0.6 kb upstream region, the 1st 879 by of the CRZ1 ORF, plus 2 stop codons) in front of the ALG3 terminator sequence, followed by the lacZ-URA5-lacZ URAblaster, and then connected to a 2 kb genomic DNA fragment containing the last 234 by of the CRZ1 ORF plus 1.7 kb of the downstream region. Homologous recombination-mediated double-crossovers between the SfiI-fragment of pGLY12832 (FIG. 7) and the chromosomal CRZ1 region replaced the endogenous CRZ1 ORF with a truncated version of CRZ1 with only the first 294 amino acid residues.

After confirming that the DNA constructs precisely replaced the endogenous CRZ1 gene with the corresponding deletion or truncations, their abilities to grow at 35° C. on solid media and 32° C. in liquid media in a bioreactor was examined. It was confirmed that these CRZ14 truncation and deletion mutants displayed temperature-resistant phenotypes very similar to those observed from the original mutants isolated by UV mutagenesis.

Figure 9:
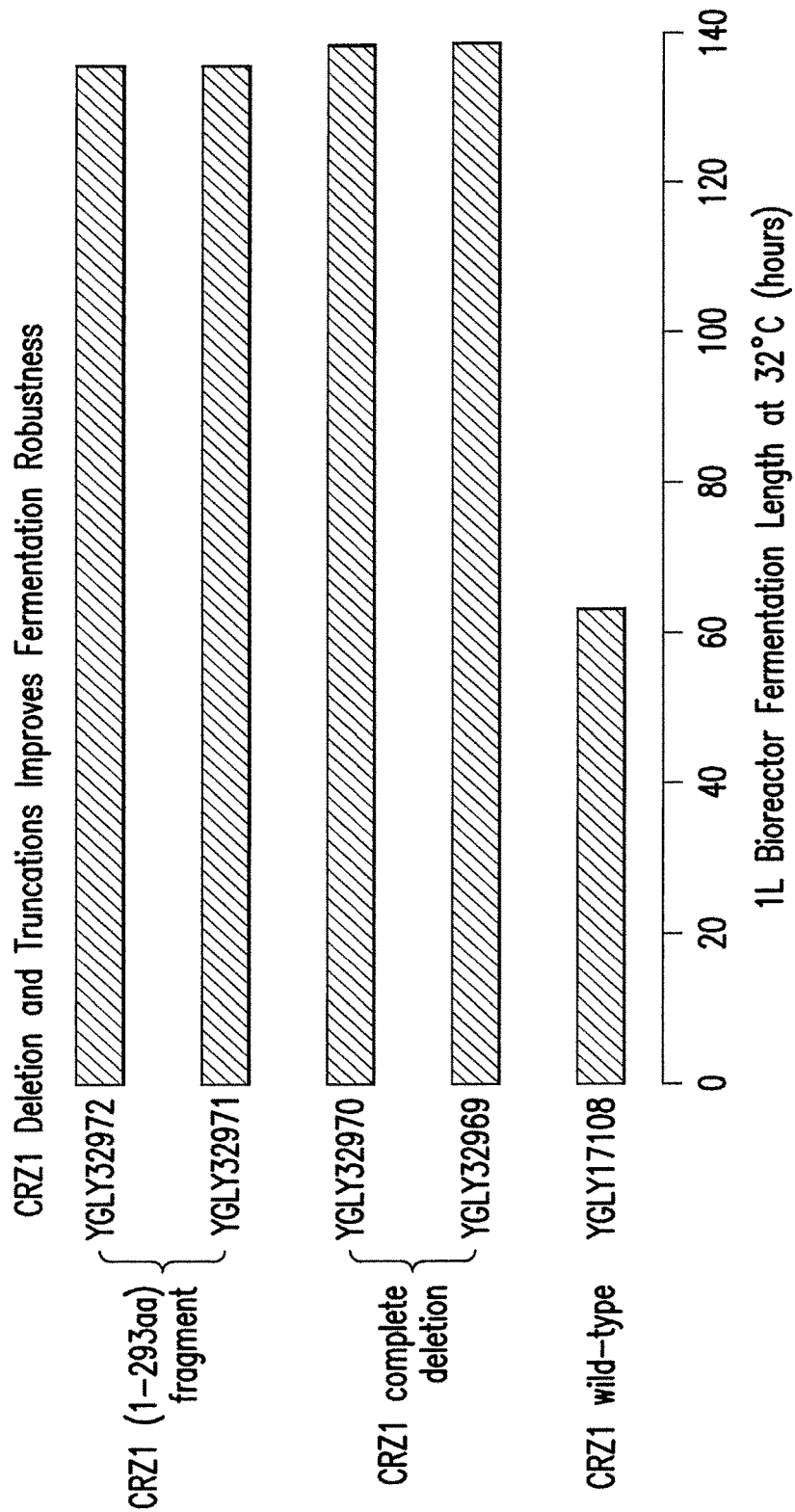
FIG. 9: *Pichia pastoris* CRZ1 deletion and truncation mutants exhibited improved fermentation robustness at 32° C.

Next, the truncation and deletion mutants were subjected to standard DasGip MeOH fed-batch fermentation runs (Hopkins et al., 2011) to determine whether they would also display increased fermentation robustness at 32° C. As shown in FIG. 9, the YGLY17108 control strain displayed heavy lysis and was not viable within 65 hours of MeOH induction at 32° C. In contrast, the strains harboring the complete deletion and truncations of the CRZ1 gene showed a remarkable increase in fermentation robustness and successfully completed more than 130 hours of MeOH induction. These results demonstrated that CRZ1 in-activation, by deleting the CRZ1 ORF completely or partially, is sufficient for improving the fermentation robustness of glyco-engineered strains. Furthermore, the phenotypes exhibited by these directed gene-replacement strains closely resembled those displayed by the corresponding UV-induced mutants, illustrating that the mutations within the CRZ1 gene were responsible for the improved thermal tolerance and fermentation robustness observed from the UV-induced mutants.

Figure 10:
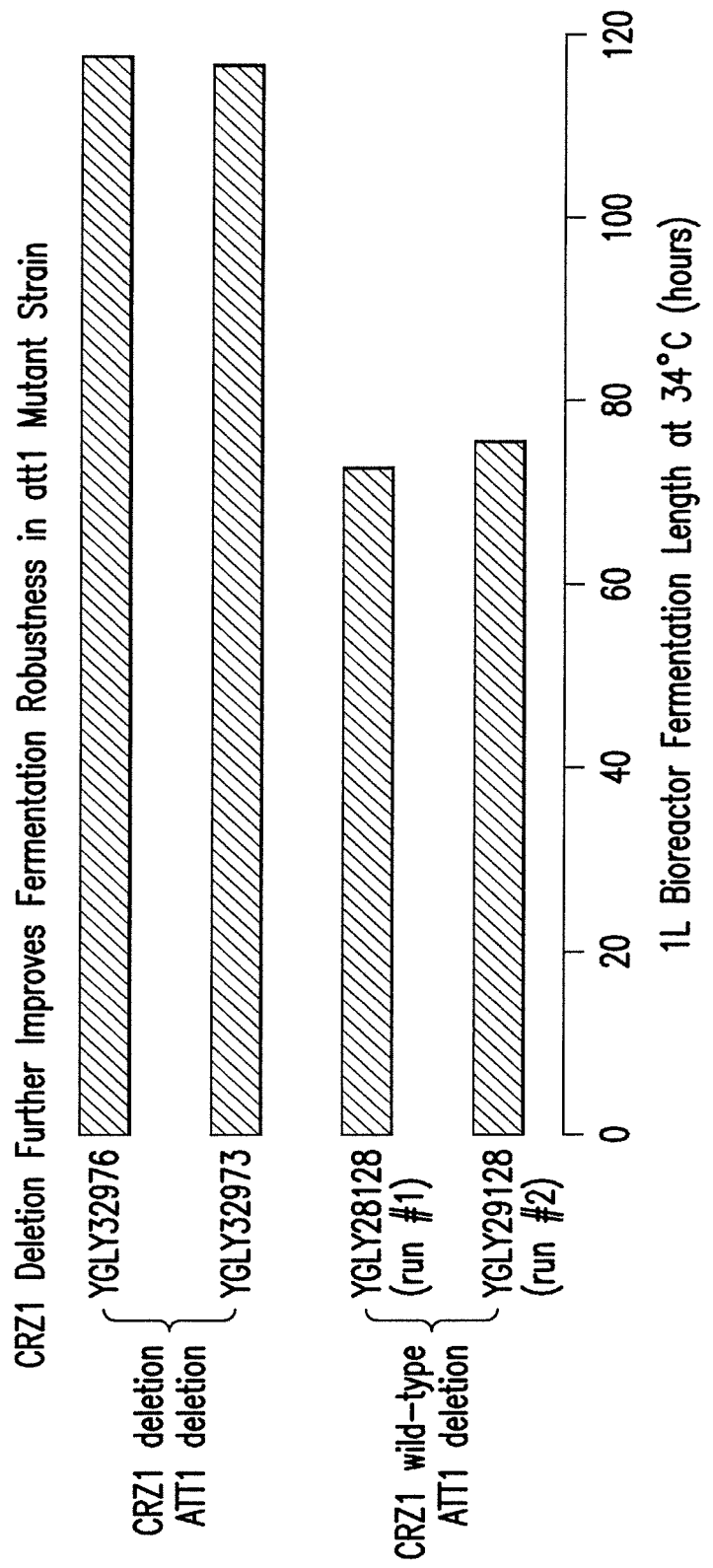
FIG. 10: *Pichia pastoris* CRZ1 deletion further improves fermentation robustness in an att1 mutant strain at 34° C.

Inactivation of the ATT1 gene has resulted in a dramatic improvement in strain fermentation robustness. Because the inactivation of CRZ1 and ATT1 gave rise to very similar phenotype (i.e., temperature-resistance and enhanced fermentation robustness), we want to examine if CRZ1 deletion would further improve the fermentation robustness of a strain already containing an ATT1 deletion mutation. To this end, we constructed crz1, att1 double deletion mutants and tested their fermentation robustness by carrying out standard MeOH fed-batch fermentation runs in 1 L DasGip bioreactors at 34° C. Under this very stringent fermentation condition, the att1 single deletion strain YGLY29128 remained viable for 75 hours, whereas the crz1, att1 double mutants remained viable for more than 115 hours (FIG. 10). These results clearly demonstrated that the fermentation robustness improvements derived from att1 deletion and crz1 deletion are additive, and that crz1, att1 double mutants displayed much higher level of fermentation robustness than the single mutants.

REFERENCES

Barnard G C, Kull A R, Sharkey N S, Shaikh S S, Rittenhour A M, Burnina I, Jiang Y, Li F, Lynaugh H, Mitchell T, Nett J H, Nylen A, Potgieter T I, Prinz B, Rios S E, Zha D, Sethuraman N, Stadheim T A, Bobrowicz P (2010) High-throughput screening and selection of yeast cell lines expressing monoclonal antibodies. J. Ind. Microbiol. Biotechnol. 37(9):961-71

Bobrowicz P, Davidson R C, Li H, Potgieter T I, Nett J H, Hamilton S R, Stadheim T A, Miele R G, Bobrowicz B, Mitchell T, Rausch S, Renfer E, Wildt S (2004) Engineering of an artificial glycosylation pathway blocked in core oligosaccharide assembly in the yeast Pichia pastoris: production of complex humanized glycoproteins with terminal galactose. Glycobiology 14(9):757-66.

Choi B K, Bobrowicz P, Davidson R C, Hamilton S R, Kung D H, Li H, Miele R G, Nett J H, Wildt S, Gerngross T U (2003) Use of combinatorial genetic libraries to humanize N-linked glycosylation in the yeast Pichia pastoris. Proc Natl Acad Sci USA. 100(9):5022-7.

Hamilton S R, Davidson R C, Sethuraman N, Nett J H, Jiang Y, Rios S, Bobrowicz P, Stadheim T A, Li H, Choi B K, Hopkins D, Wischnewski H, Roser J, Mitchell T, Strawbridge R R, Hoopes J, Wildt S, Gerngross TU (2006) Humanization of yeast to produce complex terminally sialylated glycoproteins. Science 313(5792):1441-3

Jiang Y, Li F, Zha D, Potgieter T I, Mitchell T, Moore R, Cukan M, Houston-Cummings N R, Nylen A, Drummond J E, McKelvey T W, d'Anjou M, Stadheim T A, Sethuraman N, Li H. Purification process development of a recombinant monoclonal antibody expressed in glycoengineered Pichia pastoris. Protein Expr Purif. 2011 March; 76(1):7-14. Epub 2010 Nov. 11. PubMed PMID: 21074617.

Li H, Sethuraman N, Stadheim T A, Zha D, Prinz B, Ballew N, Bobrowicz P, Choi B K, Cook W J, Cukan M, Houston-Cummings N R, Davidson R, Gong B, Hamilton S R, Hoopes J P, Jiang Y, Kim N, Mansfield R, Nett J H, Rios S, Strawbridge R, Wildt S, Gerngross T U (2006) Optimization of humanized IgGs in glycoengineered Pichia pastoris. Nat Biotechnol. 24(2):210-5.

Potgieter T I, Cukan M, Drummond J E, Houston-Cummings N R, Jiang Y, Li F, Lynaugh H, Mallem M, McKelvey T W, Mitchell T, Nylen A, Rittenhour A, Stadheim T A, Zha D, d'Anjou M. (2009) Production of monoclonal antibodies by glycoengineered Pichia pastoris. J. Biotechnol. 139(4):318-25.

Traven A, Jelicic B, Sopta M. (2006) Yeast GAL4: a transcriptional paradigm revisited. EMBO Rep. 7(5):496-9.

Winston F (2008) EMS and UV Mutagenesis in Yeast. Curr. Protoc. Mol. Biol. 82:13.3B.1-13.3B.5

Wurm F M. Production of recombinant protein therapeutics in cultivated mammalian cells. Nat Biotechnol. 2004 November; 22(11):1393-8. Review. PubMed PMID: 15529164.

Zhang N, Liu L, Dan Dumitru C, Cummings N R, Cukan M, Jiang Y, Li Y, Li F, Mitchell T, Mallem M R, Ou Y, Patel R N, Vo K, Vo K, Wang H, Burnina I, Choi B K, Huber H E, Stadheim T A, Zha D. Glycoengineered Pichia produced anti-HER2 is comparable to trastuzumab in preclinical study. MAbs. 2011 May 1; 3(3). [Epub ahead of print] PubMed PMID: 21487242.

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An isolated fungal host cell lacking a functional CRZ1 polypeptide with the proviso that the cell comprises a functional ATT1 polypeptide
    wherein the endogenous CRZ1 gene encodes an endogenous CRZ1 polypeptide that differs from a wild-type CRZ1 polypeptide comprising the amino acid sequence set forth in SEQ ID NO: 3 in that the endogenous CRZ1 polypeptide comprises the mutation L294→STOP and wherein the fungal host cell is *Pichia pastoris* comprising a mutated, disrupted, truncated or partially or fully deleted endogenous OCH1.

2. The isolated fungal host cell of claim 1:
    (i) wherein one or more endogenous beta-mannosyltransferase genes of the isolated fungal host cell are mutated, disrupted, truncated or partially or fully deleted;
    (ii) wherein the isolated fungal host cell comprises comprising a polynucleotide encoding an alpha-1,2 mannosidase enzyme;
    (iii) wherein one or more endogenous phosphomannosyl transferases of the isolated fungal host cell are mutated, disrupted, truncated or partially or fully deleted;
    (iv) wherein the isolated fungal host cell comprises comprising a single-subunit oligosaccharyltransferase;
    (v) wherein endogenous ALG3 of the isolated fungal host cell is mutated, disrupted, truncated or partially or fully deleted;
    (vi) wherein the isolated fungal host cell comprises a polynucleotide encoding an endomannosidase;
    (vii) wherein the isolated fungal host cell comprises one or more polynucleotides encoding a bifunctional UDP-N-acetylglucosamine-2-epimerase/N-acetylmannosamine kinase, an N-acetylneuraminate-9-phosphate synthase, or a CMP-sialic acid synthase;
    (viii) comprising a polynucleotide encoding galactosyltransferase;
    (ix) comprising a polynucleotide encoding nucleotide sugar transporter;
    comprising a polynucleotide encoding sialyltransferase;
    (xi) comprising a polynucleotide encoding acetylglucosaminyl transferase; or
    (xii) wherein one or more endogenous proteases are mutated, disrupted, truncated or partially or fully deleted.

3. The isolated fungal host cell of claim 1 comprising a heterologous polynucleotide that encodes a heterologous polypeptide.

4. The isolated fungal host cell of claim 2, wherein the heterologous polypeptide is an immunoglobulin.

* * * * *

SEQUENCE LISTING

```
<160> NUMBER OF SEQ ID NOS: 9

<210> SEQ ID NO 1
<211> LENGTH: 676
<212> TYPE: PRT
<213> ORGANISM: Saccharomyces cerevisiae

<400> SEQUENCE: 1

Met Ser Phe Ser Asn Gly Asn Met Ala Ser Tyr Met Thr Ser Ser Asn
1               5                   10                  15

Gly Glu Glu Gln Ser Ile Asn Asn Lys Asn Asp Ile Asp Asp Asn Ser
            20                  25                  30

Ala Tyr Arg Arg Asn Asn Phe Arg Asn Ser Ser Asn Ser Gly Ser His
        35                  40                  45

Thr Phe Gln Leu Ser Asp Leu Asp Leu Asp Val Asp Met Arg Met Asp
    50                  55                  60

Ser Ala Asn Ser Ser Glu Lys Ile Ser Lys Asn Leu Ser Ser Gly Ile
65                  70                  75                  80
```

```
Pro Asp Ser Phe Asp Ser Asn Val Asn Ser Leu Leu Ser Pro Ser Ser
                 85                  90                  95

Gly Ser Tyr Ser Ala Asp Leu Asn Tyr Gln Ser Leu Tyr Lys Pro Asp
            100                 105                 110

Leu Pro Gln Gln Gln Leu Gln Gln Gln Gln Gln Gln Gln Gln Gln Gln
        115                 120                 125

Gln Gln Gln Gln Gln Gln Gln Lys Gln Thr Pro Thr Leu Lys Val
130                 135                 140

Glu Gln Ser Asp Thr Phe Gln Trp Asp Asp Ile Leu Thr Pro Ala Asp
145                 150                 155                 160

Asn Gln His Arg Pro Ser Leu Thr Asn Gln Phe Leu Ser Pro Arg Ser
                165                 170                 175

Asn Tyr Asp Gly Thr Thr Arg Ser Ser Gly Ile Asp Ser Asn Tyr Ser
            180                 185                 190

Asp Thr Glu Ser Asn Tyr His Thr Pro Tyr Leu Tyr Pro Gln Asp Leu
        195                 200                 205

Val Ser Ser Pro Ala Met Ser His Leu Thr Ala Asn Asn Asp Asp Phe
    210                 215                 220

Asp Asp Leu Leu Ser Val Ala Ser Met Asn Ser Asn Tyr Leu Leu Pro
225                 230                 235                 240

Val Asn Ser His Gly Tyr Lys His Ile Ser Asn Leu Asp Glu Leu Asp
                245                 250                 255

Asp Leu Leu Ser Leu Thr Tyr Ser Asp Asn Asn Leu Leu Ser Ala Ser
            260                 265                 270

Asn Asn Ser Asp Phe Asn Asn Ser Asn Asn Gly Ile Ile Asn Thr Ala
        275                 280                 285

Asp Thr Gln Asn Ser Thr Ile Ala Ile Asn Lys Ser Lys Val Gly Thr
290                 295                 300

Asn Gln Lys Met Leu Leu Thr Ile Pro Thr Ser Ser Thr Pro Ser Pro
305                 310                 315                 320

Ser Thr His Ala Ala Pro Val Thr Pro Ile Ile Ser Ile Gln Glu Phe
                325                 330                 335

Asn Glu Gly His Phe Pro Val Lys Asn Glu Asp Gly Thr Leu Gln
            340                 345                 350

Leu Lys Val Arg Asp Asn Glu Ser Tyr Ser Ala Thr Asn Asn Asn Asn
        355                 360                 365

Leu Leu Arg Pro Asp Asp Asn Asp Tyr Asn Asn Glu Ala Leu Ser Asp
    370                 375                 380

Ile Asp Arg Ser Phe Glu Asp Ile Ile Asn Gly Arg Lys Leu Lys Leu
385                 390                 395                 400

Lys Lys Ser Arg Arg Ser Ser Gln Thr Ser Asn Asn Ser Phe Thr
                405                 410                 415

Ser Arg Arg Ser Ser Arg Ser Arg Ser Ile Ser Pro Asp Glu Lys Ala
            420                 425                 430

Lys Ser Ile Ser Ala Asn Arg Glu Lys Leu Leu Glu Met Ala Asp Leu
        435                 440                 445

Leu Pro Ser Ser Glu Asn Asp Asn Asn Arg Glu Arg Tyr Asp Asn Asp
    450                 455                 460

Ser Lys Thr Ser Tyr Asn Thr Ile Asn Ser Ser Asn Phe Asn Glu Asp
465                 470                 475                 480

Asn Asn Asn Asn Asn Leu Leu Thr Ser Lys Pro Lys Ile Glu Ser Gly
                485                 490                 495
```

-continued

```
Ile Val Asn Ile Lys Asn Glu Leu Asp Asp Thr Ser Lys Asp Leu Gly
            500                 505                 510

Ile Leu Leu Asp Ile Asp Ser Leu Gly Gln Phe Glu Gln Lys Val Gly
        515                 520                 525

Phe Lys Asn Asp Asp Asn His Glu Asn Asn Asp Asn Gly Thr Phe Ser
    530                 535                 540

Val Lys Lys Asn Asp Asn Leu Glu Lys Leu Asp Ser Val Thr Asn Asn
545                 550                 555                 560

Arg Lys Asn Pro Ala Asn Phe Ala Cys Asp Val Cys Gly Lys Lys Phe
                565                 570                 575

Thr Arg Pro Tyr Asn Leu Lys Ser His Leu Arg Thr His Thr Asn Glu
            580                 585                 590

Arg Pro Phe Ile Cys Ser Ile Cys Gly Lys Ala Phe Ala Arg Gln His
        595                 600                 605

Asp Arg Lys Arg His Glu Asp Leu His Thr Gly Lys Lys Arg Tyr Val
    610                 615                 620

Cys Gly Gly Lys Leu Lys Asp Gly Lys Pro Trp Gly Cys Gly Lys Lys
625                 630                 635                 640

Phe Ala Arg Ser Asp Ala Leu Gly Arg His Phe Lys Thr Glu Ser Gly
                645                 650                 655

Arg Arg Cys Ile Thr Pro Leu Tyr Glu Glu Ala Arg Gln Glu Lys Ser
            660                 665                 670

Gly Gln Glu Ser
        675
```

```
<210> SEQ ID NO 2
<211> LENGTH: 1557
<212> TYPE: DNA
<213> ORGANISM: Pichia pastoris
<220> FEATURE:
<221> NAME/KEY: CDS
<222> LOCATION: (1)..(1557)

<400> SEQUENCE: 2
```

```
atg gca gac caa cgg ctt gag gat gag ttt gat atc tcc aga tac tta      48
Met Ala Asp Gln Arg Leu Glu Asp Glu Phe Asp Ile Ser Arg Tyr Leu
1               5                   10                  15 tct att tct cct atc gag tca gct tca atc gaa gaa tca atc aac ggt      96
Ser Ile Ser Pro Ile Glu Ser Ala Ser Ile Glu Glu Ser Ile Asn Gly
            20                  25                  30 tta atg agt agt tgg att cct ccg gct aag ggt gag att aga gat tca     144
Leu Met Ser Ser Trp Ile Pro Pro Ala Lys Gly Glu Ile Arg Asp Ser
        35                  40                  45 ctt cct cca aac gct tct ttt gaa gct aca gac agt ttt tca acc agt     192
Leu Pro Pro Asn Ala Ser Phe Glu Ala Thr Asp Ser Phe Ser Thr Ser
    50                  55                  60 tca tac cag gaa att ata cca gca cag gtg aaa ata aaa ctg gag ttt     240
Ser Tyr Gln Glu Ile Ile Pro Ala Gln Val Lys Ile Lys Leu Glu Phe
65                  70                  75                  80 gat aat gac cag cag cct gtt ttc tat caa gaa tcg caa cca gtt tat     288
Asp Asn Asp Gln Gln Pro Val Phe Tyr Gln Glu Ser Gln Pro Val Tyr
                85                  90                  95 gat aag cat tta acc gtc aat gat cag gaa acc aga agc gcc caa gac     336
Asp Lys His Leu Thr Val Asn Asp Gln Glu Thr Arg Ser Ala Gln Asp
            100                 105                 110 ttc aac caa tac ttg aat gct gat gcc gta tcg agg acc aac tcc atc     384
Phe Asn Gln Tyr Leu Asn Ala Asp Ala Val Ser Arg Thr Asn Ser Ile
        115                 120                 125
```

| | | |
|---|---|---|
| tcc aac tta tcg gag ctg tca act cat tcc cat att acc cct cca acg<br>Ser Asn Leu Ser Glu Leu Ser Thr His Ser His Ile Thr Pro Pro Thr<br>130                135                140 | 432 | |
| cta ctt cat gat caa gcc tca ttg tct cct gct ctc tta tct atg aac<br>Leu Leu His Asp Gln Ala Ser Leu Ser Pro Ala Leu Leu Ser Met Asn<br>145                150              155            160 | 480 | |
| agt gat gaa aga aac gaa ctc aat ctg gaa aca cta cag cta gat caa<br>Ser Asp Glu Arg Asn Glu Leu Asn Leu Glu Thr Leu Gln Leu Asp Gln<br>                165              170              175 | 528 | |
| acg tca cag cct tac gtg aat cag ata aaa acg gag gca gct tac gaa<br>Thr Ser Gln Pro Tyr Val Asn Gln Ile Lys Thr Glu Ala Ala Tyr Glu<br>            180              185              190 | 576 | |
| gag ctt tca gag tta cac cac aga tta gaa aga ctc act gag aca aat<br>Glu Leu Ser Glu Leu His His Arg Leu Glu Arg Leu Thr Glu Thr Asn<br>       195             200              205 | 624 | |
| tta att cat caa gac cag ctt caa ctc gaa caa caa gag caa caa aat<br>Leu Ile His Gln Asp Gln Leu Gln Leu Glu Gln Gln Glu Gln Gln Asn<br>210                215              220 | 672 | |
| cag act cct cat act ctc agt cct cct ata caa ctt cag act ccc ata<br>Gln Thr Pro His Thr Leu Ser Pro Pro Ile Gln Leu Gln Thr Pro Ile<br>225                230              235            240 | 720 | |
| atc aaa gtc ttg caa gcc cca aat gat ata gca gca aat acc ccg tct<br>Ile Lys Val Leu Gln Ala Pro Asn Asp Ile Ala Ala Asn Thr Pro Ser<br>                245              250              255 | 768 | |
| ctt ttt tct caa tct aac cat tca tct cca tat aac aca ccc aaa cat<br>Leu Phe Ser Gln Ser Asn His Ser Ser Pro Tyr Asn Thr Pro Lys His<br>            260              265              270 | 816 | |
| tcc agg tca aac tcg ttg agt tca aat gac aga caa cat gat att cca<br>Ser Arg Ser Asn Ser Leu Ser Ser Asn Asp Arg Gln His Asp Ile Pro<br>       275             280              285 | 864 | |
| caa ata tcc tca gtt tta gac acg tct tcg ttt ttg gta cct gga gat<br>Gln Ile Ser Ser Val Leu Asp Thr Ser Ser Phe Leu Val Pro Gly Asp<br>290                295              300 | 912 | |
| cag ttt caa gca atg aga gaa ggt aga cag agg agg aaa tcc gag tcc<br>Gln Phe Gln Ala Met Arg Glu Gly Arg Gln Arg Arg Lys Ser Glu Ser<br>305                310              315            320 | 960 | |
| aac tct aga aac tcg aaa gaa cgt tct aaa tct agg gaa ccg cca aag<br>Asn Ser Arg Asn Ser Lys Glu Arg Ser Lys Ser Arg Glu Pro Pro Lys<br>            325              330              335 | 1008 | |
| tcc agg tct aga tct aga gac agt gca aca gat cat cat atg gaa gtt<br>Ser Arg Ser Arg Ser Arg Asp Ser Ala Thr Asp His His Met Glu Val<br>                340              345              350 | 1056 | |
| atg agc aga gaa aag act ctt gag ttg gca gct tct cag cca agc tcc<br>Met Ser Arg Glu Lys Thr Leu Glu Leu Ala Ala Ser Gln Pro Ser Ser<br>355                360              365 | 1104 | |
| aag acg ccg caa aag aac cct tcc atc tat gct tgc tcg ctc tgc tcc<br>Lys Thr Pro Gln Lys Asn Pro Ser Ile Tyr Ala Cys Ser Leu Cys Ser<br>370                375              380 | 1152 | |
| aag aga ttc aca aga cca tat aat ttg aag tct cac ctt cgc acg cac<br>Lys Arg Phe Thr Arg Pro Tyr Asn Leu Lys Ser His Leu Arg Thr His<br>385                390              395            400 | 1200 | |
| gct gat gaa agg cct ttc cag tgt tca ata tgc ggg aag gca ttt gct<br>Ala Asp Glu Arg Pro Phe Gln Cys Ser Ile Cys Gly Lys Ala Phe Ala<br>                405              410              415 | 1248 | |
| cgt tct cac gac aga aag cgt cat gag gat ctg cat agt ggt gaa cga<br>Arg Ser His Asp Arg Lys Arg His Glu Asp Leu His Ser Gly Glu Arg<br>            420              425              430 | 1296 | |
| aag tat tgc tgc aaa ggt gtt ttg tct gac gga gta act aca tgg ggc<br>Lys Tyr Cys Cys Lys Gly Val Leu Ser Asp Gly Val Thr Thr Trp Gly<br>                435              440              445 | 1344 | |

```
tgt gaa aaa aga ttt gcc cga aca gat gcg ctg ggt aga cat ttc aaa      1392
Cys Glu Lys Arg Phe Ala Arg Thr Asp Ala Leu Gly Arg His Phe Lys
    450                 455                 460 act gaa tgt ggt aaa ctg tgt atc aag ccg ctg atg gat gaa cta aag      1440
Thr Glu Cys Gly Lys Leu Cys Ile Lys Pro Leu Met Asp Glu Leu Lys
465                 470                 475                 480 agg gag gaa gct tac agg agg aat gaa cca gta aca gaa atg aat gac      1488
Arg Glu Glu Ala Tyr Arg Arg Asn Glu Pro Val Thr Glu Met Asn Asp
                485                 490                 495 gag ctt tac tcc caa tct gtc caa gat ata ttt agc tct cag cgg ctt      1536
Glu Leu Tyr Ser Gln Ser Val Gln Asp Ile Phe Ser Ser Gln Arg Leu
            500                 505                 510 ggt cag aac ata gat gac tga                                          1557
Gly Gln Asn Ile Asp Asp
        515

<210> SEQ ID NO 3
<211> LENGTH: 518
<212> TYPE: PRT
<213> ORGANISM: Pichia pastoris

<400> SEQUENCE: 3

Met Ala Asp Gln Arg Leu Glu Asp Glu Phe Asp Ile Ser Arg Tyr Leu
1               5                   10                  15

Ser Ile Ser Pro Ile Glu Ser Ala Ser Ile Glu Glu Ser Ile Asn Gly
            20                  25                  30

Leu Met Ser Ser Trp Ile Pro Pro Ala Lys Gly Glu Ile Arg Asp Ser
        35                  40                  45

Leu Pro Pro Asn Ala Ser Phe Glu Ala Thr Asp Ser Phe Ser Thr Ser
50                  55                  60

Ser Tyr Gln Glu Ile Ile Pro Ala Gln Val Lys Ile Lys Leu Glu Phe
65                  70                  75                  80

Asp Asn Asp Gln Gln Pro Val Phe Tyr Gln Glu Ser Gln Pro Val Tyr
                85                  90                  95

Asp Lys His Leu Thr Val Asn Asp Gln Glu Thr Arg Ser Ala Gln Asp
            100                 105                 110

Phe Asn Gln Tyr Leu Asn Ala Asp Ala Val Ser Arg Thr Asn Ser Ile
        115                 120                 125

Ser Asn Leu Ser Glu Leu Ser Thr His Ser His Ile Thr Pro Pro Thr
    130                 135                 140

Leu Leu His Asp Gln Ala Ser Leu Ser Pro Ala Leu Leu Ser Met Asn
145                 150                 155                 160

Ser Asp Glu Arg Asn Glu Leu Asn Leu Glu Thr Leu Gln Leu Asp Gln
                165                 170                 175

Thr Ser Gln Pro Tyr Val Asn Gln Ile Lys Thr Glu Ala Ala Tyr Glu
            180                 185                 190

Glu Leu Ser Glu Leu His His Arg Leu Glu Arg Leu Thr Glu Thr Asn
        195                 200                 205

Leu Ile His Gln Asp Gln Leu Gln Leu Glu Gln Gln Glu Gln Gln Asn
    210                 215                 220

Gln Thr Pro His Thr Leu Ser Pro Pro Ile Gln Leu Gln Thr Pro Ile
225                 230                 235                 240

Ile Lys Val Leu Gln Ala Pro Asn Asp Ile Ala Ala Asn Thr Pro Ser
                245                 250                 255

Leu Phe Ser Gln Ser Asn His Ser Ser Pro Tyr Asn Thr Pro Lys His
            260                 265                 270
```

Ser Arg Ser Asn Ser Leu Ser Ser Asn Asp Arg Gln His Asp Ile Pro
            275                 280                 285

Gln Ile Ser Ser Val Leu Asp Thr Ser Ser Phe Leu Val Pro Gly Asp
        290                 295                 300

Gln Phe Gln Ala Met Arg Glu Gly Arg Gln Arg Lys Ser Glu Ser
305                 310                 315                 320

Asn Ser Arg Asn Ser Lys Glu Arg Ser Lys Ser Arg Glu Pro Pro Lys
                325                 330                 335

Ser Arg Ser Arg Ser Arg Asp Ser Ala Thr Asp His His Met Glu Val
            340                 345                 350

Met Ser Arg Glu Lys Thr Leu Glu Leu Ala Ala Ser Gln Pro Ser Ser
            355                 360                 365

Lys Thr Pro Gln Lys Asn Pro Ser Ile Tyr Ala Cys Ser Leu Cys Ser
        370                 375                 380

Lys Arg Phe Thr Arg Pro Tyr Asn Leu Lys Ser His Leu Arg Thr His
385                 390                 395                 400

Ala Asp Glu Arg Pro Phe Gln Cys Ser Ile Cys Gly Lys Ala Phe Ala
                405                 410                 415

Arg Ser His Asp Arg Lys Arg His Glu Asp Leu His Ser Gly Glu Arg
            420                 425                 430

Lys Tyr Cys Cys Lys Gly Val Leu Ser Asp Gly Val Thr Thr Trp Gly
        435                 440                 445

Cys Glu Lys Arg Phe Ala Arg Thr Asp Ala Leu Gly Arg His Phe Lys
450                 455                 460

Thr Glu Cys Gly Lys Leu Cys Ile Lys Pro Leu Met Asp Glu Leu Lys
465                 470                 475                 480

Arg Glu Glu Ala Tyr Arg Arg Asn Glu Pro Val Thr Glu Met Asn Asp
                485                 490                 495

Glu Leu Tyr Ser Gln Ser Val Gln Asp Ile Phe Ser Ser Gln Arg Leu
            500                 505                 510

Gly Gln Asn Ile Asp Asp
        515

<210> SEQ ID NO 4
<211> LENGTH: 19
<212> TYPE: DNA
<213> ORGANISM: Artificial Sequence
<220> FEATURE:
<223> OTHER INFORMATION: Pichia pastoris

<400> SEQUENCE: 4
gtatgcgata tagtgtgga                                              19

<210> SEQ ID NO 5
<211> LENGTH: 19
<212> TYPE: DNA
<213> ORGANISM: Artificial Sequence
<220> FEATURE:
<223> OTHER INFORMATION: Pichia pastoris

<400> SEQUENCE: 5
tggggagaag gtaccgaag                                              19

<210> SEQ ID NO 6
<211> LENGTH: 20
<212> TYPE: DNA
<213> ORGANISM: Artificial Sequence
<220> FEATURE:

```
<223> OTHER INFORMATION: primer

<400> SEQUENCE: 6
cactacgcgt actgtgagcc                                               20

<210> SEQ ID NO 7
<211> LENGTH: 20
<212> TYPE: DNA
<213> ORGANISM: Artificial Sequence
<220> FEATURE:
<223> OTHER INFORMATION: Pichia pastoris

<400> SEQUENCE: 7
aggatatcaa acccgaccag                                               20

<210> SEQ ID NO 8
<211> LENGTH: 20
<212> TYPE: DNA
<213> ORGANISM: Artificial Sequence
<220> FEATURE:
<223> OTHER INFORMATION: Pichia pastoris

<400> SEQUENCE: 8
gacacatgcg aaatgtcctg                                               20

<210> SEQ ID NO 9
<211> LENGTH: 20
<212> TYPE: DNA
<213> ORGANISM: Artificial Sequence
<220> FEATURE:
<223> OTHER INFORMATION: Pichia pastoris

<400> SEQUENCE: 9
ttgagttggc agcttctcag                                               20
```